US009965586B2

(12) United States Patent
Schuller et al.

(10) Patent No.: US 9,965,586 B2
(45) Date of Patent: May 8, 2018

(54) NOISE REDUCTION METHODS FOR NUCLEIC ACID AND MACROMOLECULE SEQUENCING

(71) Applicants: The Regents of the University of California, Oakland, CA (US); Los Alamos National Laboratory, Los Alamos, NM (US)

(72) Inventors: Ivan K. Schuller, San Diego, CA (US); Massimiliano Di Ventra, Carlsbad, CA (US); Alexander Balatsky, Santa Fe, NM (US)

(73) Assignees: The Regents of the University of California, Oakland, CA (US); Los Alamos National Laboratory, Los Alamos, NM (US)

( * ) Notice: Subject to any disclaimer, the term of this patent is extended or adjusted under 35 U.S.C. 154(b) by 65 days.

(21) Appl. No.: 14/664,738

(22) Filed: Mar. 20, 2015

(65) Prior Publication Data

US 2015/0347675 A1 Dec. 3, 2015

Related U.S. Application Data

(60) Provisional application No. 61/968,280, filed on Mar. 20, 2014.

(51) Int. Cl.
*G01N 33/48* (2006.01)
*G06F 19/22* (2011.01)
*G06G 7/58* (2006.01)

(52) U.S. Cl.
CPC .................................. *G06F 19/22* (2013.01)

(58) Field of Classification Search
None
See application file for complete search history.

(56) References Cited

PUBLICATIONS

Zwolak, M., "Colloquium: Physical approaches to DNA sequencing and detection", Rev. Mod. Phys., vol. 80, No. 1, Jan.-Mar. 2008, pp. 141-165.
Eid, John et al., "Real-Time DNA Sequencing from Single Polymerase Molecules", Science, vol. 323, Jan. 2, 2009, 7 pages.
Quail, Michael A. et al., "A tale of three next generation sequencing platforms: comparison of Ion Torrent, Pacific Biosciences and Illumina MiSeq sequencers", BMC Genomics 2012, 13:341, pp. 1-13.
Rusk, Nicole, "Torrents of sequence", vol. 8, No. 1, Jan. 2011, 1 page.
Tsutsui, Makusu et al., "Formation and Self-Breaking Mechanism of Stable Atom-Sized Junctions", Nano Lett., vol. 8, No. 1, 2008, pp. 345-349.
Tsutsui, Makusu et al., "Electrical Detection of Single Methylcytosines in a DNA Oligomer", Am. Chem. Soc. 2011, 133, pp. 9124-9128.
Krems, Matt et al., "Effect of Noise on DNA Sequencing via Transverse Electronic Transport", Biophysical Journal, vol. 97, Oct. 2009, pp. 1990-1995.
Murphy, M. C. et al., "Probing Single-Stranded DNA Conformational Flexibility Using Fluorescence Spectroscopy", Biophysical Journal, vol. 86, Apr. 2004, pp. 2530-2537.
He, Yuhui et al., "Controlling DNA Translocation through Gate Modulation of Nanopore Wall Surface Charges", www.acsnano.org, vol. 5, No. 7, pp. 5509-5518, 2011.
Huang, Shuo et al., "Identifying single bases in a DNA oligomer with electron tunnelling", Nature Nanotechnology, vol. 5, Nov. 14, 2010, pp. 868-873.
Phillips, J. C. et al., "Scalable Molecular Dynamics with NAMD", Journal of Computational Chemistry, vol. 26, No. 16, pp. 1781-1802, 2005.
Pecchia, A. et al., "Role of thermal vibrations in molecular wire conduction", Physical Review B 68, 235321 (2003), 12 pages.
Mitra, S. et al., "Dynamics of water in confined space (porous alumina): QENS study", J. Phys.: Condens. Matter 13 (2001), pp. 8455-8465.
Fenton, Lawrence F., "The Sum of Log-Normal Probability Distributions in Scatter Transmission Systems", Ire Transactions on ICommunications Systems, 11 pages.
Mardis, Elaine R., "A decade's perspective on DNA sequencing technology", Nature, vol. 470, Feb. 10, 2011, pp. 198-203.
Tichoniuk, Mariusz et al., "Application of DNA Hybridization Biosensor as a Screening Method for the Detection of Genetically Modified Food Components", Sensors 2008, 8, pp. 2118-2135.
Savolainen, Vincent et al., "Towards writing the encyclopaedia of life: an introduction to DNA barcoding", Phil. Trans. R. Soc. B (2005) 360, pp. 1805-1811.
Liu, Zhuang et al., "PEGylated Nanographene Oxide for Delivery of Water-Insoluble Cancer Drugs", J. Am. Chem. Soc. 2008, 130, pp. 10876-10877.
Lorenz, Joseph G. et al., "The problems and promise of DNA barcodes for species diagnosis of primate biomaterials", Phil. Trans. R. Soc. B (2005) 360, pp. 1869-1877.
Cook, Victoria J. et al., "Conventional Methods versus 16S Ribosomal DNA Sequencing for Identification of Nontuberculous Mycobacteria: Cost Analysis", Journal of Clinical Microbiology, Mar. 2003, vol. 41, No. 3, pp. 1010-1015.
Lagerqvist, Johan et al., "Fast DNA Sequencing via Transverse Electronic Transport", Nano Lett., vol. 6, No. 4, 2006, pp. 779-782.
Min, Seung Kyu et al., "Fast DNA sequencing with a graphene-based nanochannel device", Nature Nanotechnology, vol. 6, Mar. 2011, pp. 162-165.

(Continued)

*Primary Examiner* — Eric S DeJong
(74) *Attorney, Agent, or Firm* — Perkins Coie LLP

(57) ABSTRACT

Methods, systems, and devices are disclosed for processing macromolecule sequencing data with substantial noise reduction. In one aspect, a method for reducing noise in a sequential measurement of a macromolecule comprising serial subunits includes cross-correlating multiple measured signals of a physical property of subunits of interest of the macromolecule, the multiple measured signals including the time data associated with the measurement of the signal, to remove or at least reduce signal noise that is not in the same frequency and in phase with the systematic signal contribution of the measured signals.

15 Claims, 11 Drawing Sheets

(56) References Cited

PUBLICATIONS

Seong, Gi Hun et al., "Single-Molecular AFM Probing of Specific DNA Sequencing Using RecA-Promoted. Homologous Pairing and Strand Exchange", Anal. Chem., vol. 72, No. 6, Mar. 15, 2000, pp. 1288-1293.

Clemmer, Carol R. et al., "Graphite: A Mimic for DNA and Other Biomolecules in Scanning Tunneling Microscope Studies", Science, vol. 251, p. 640.

Neto, A. H. Castro et al., "The electronic properties of graphene", Reviews of Modern Physics, vol. 81, No. 1, Jan.-Mar. 2009, pp. 109-162.

Gruneis, A et al., "Angle-resolved photoemission study of the graphite intercalation compound KC8: A key to graphene", Physical Review B 80, 075431 (2009), 5 pages.

Akca, Saliha et al., "Competing Interactions in DNA Assembly on Graphene", PLoS One, vol. 6, Issue 4, Apr. 2011, 4 pages.

Geim, A. K. et al., "The rise of graphene", Nature Materials, vol. 6, Mar. 2007, pp. 183-191.

Novoselov, K. S. et al., "Electric Field Effect in Atomically Thin Carbon Films" Science, vol. 306, Oct. 22, 2004, 5 pages.

Su, Qi et al., "Composites of Graphene with Large Aromatic Molecules", Adv. Mater. 2009, 21, pp. 3191-3195.

Henkelmen, Graeme et al., "Theoretical Calculations of Dissociative Adsorption of CH4 on an Ir(111) Surface", Physical Review Letters, vol. 86, No. 4, Jan. 22, 2001, pp. 664-667.

Jurecka, Petr et al., "Benchmark database of accurate (MP2 and CCSD(T) complete basis set limit) interaction energies of small model complexes, DNA base pairs, and amino acid pairs", Phys. Chem. Chem. Phys., 2006, 8, pp. 1985-1993.

Vanpoucke, Danny E. P. et al., "Formation of Pt-induced Ge atomic nanowires on Pt/Ge(001): A density functional theory study", Physical Review B 77, 241308(R) (2008), 4 pages.

Siegel, David A. et al., "Many-body interactions in quasi-freestanding graphene", PNAS, vol. 108, No. 28, Jul. 12, 2011, pp. 11365-11369.

Kresse, G. et al., "Efficient iterative schemes for ab initio total-energy calculations using a plane-wave basis set", Physical Review B, vol. 54, No. 16, Oct. 15, 1996—II, 18 pages.

Vanderbilt, David, "Soft self-consistent pseudopotentials in a generalized eigenvalue formalism", Physical Review B, vol. 41, No. 11, Apr. 15, 1990—I, pp. 7892-7895.

Perdew, J. P. et al., "Self-interaction correction to density-functional approximations for many-electron systems", Physical Review B, vol. 23, No. 10, May 15, 1981, pp. 5048-5079.

Ahmed, T. et al., "Electronic Fingerprints of DNA Bases on Graphene," Nano Letters, 12,2012, pp. 927-93.1.

Ahmed, T. et al., "Correlation dynamics and enhanced signals for the identification of serial biomolecules and DNA bases", Nanotechnology 25 (2014) 125705, 7 pages.

Boynton, P. et al., "Improving sequencing by tunneling with multiplexing and cross-correlations," Journal of Computational Electronics, vol. 13 Issue 4, Dec. 2014, pp. 794-800.

Brandbyge, M. et al., "Conductance eigenchannels in nanocontacts," Physical Revies B 56, Dec. 15, 1997, pp. 14956-14959.

Brandbyge, M. et al., "Density-functional method for nonequilibrium electron transport", Physical Review B, 65, 2002, 17 pages.

Branton, D. et al., "The potential and challenges of nanopore sequencing," Nature Biotechnoly, Oct. 2008, pp. 1146-1153.

Chang, S. et al., "Electronic Signatures of all Four DNA Nucleosides in a Tunneling Gap," Nano Letters, 2010, pp. 1070-1075.

Di Ventra "Chapter 3—Launder Approach," M. Electrical Transport in Nanoscale Systems; Cambridge University Press, San Diego (2008), 90 pages.

Du, X. et al., "Approaching ballistic transport in suspended graphene," Nature Nanotechnology. Aug. 3, 2008, pp. 491-495.

Duplock, E. et al., "Hallmark of Perfect Graphene," Physical Review Letters, Jun. 2004, 4 pages.

Garaj, S. et al., "Graphene as a sub-nanometre transelectrode membrane," Nature, Sep. 9, 2010, 14 pages.

Kilina, S. et al., "Electronic Properties of DNA Base Molecules Adsorbed on a Metallic Surface," The Journal of Physical Chemistry C, 2007, pp. 14541-14551.

Kilina, S. et al., "Unveiling Stability Criteria of DNA-Carbon Nanotubes Constructs by Scanning Tunneling Microscopy and Computational Modeling," Journal of Drug Delivery, 2011, Article ID 415621, 10 pages.

Lee, C. et al., Measurement of the Elastic Properties and Intrinsic Strength of Monolayer Graphene, Science 321, 2008, pp. 385-388.

He Y. et al. "Enhanced DNA Sequencing Performance Through Edge-Hydrogenation of Graphene Electrodes," Advanced Functional Materials, 2011. pp. 2674-2679.

Merchant, C. A. et al., "DNA Translocation through Graphene Nanopores," Nano Letters, 2010, pp. 2915-2292.

Postma, H, "Rapid Sequencing of Individual DNA Molecules in Graphene Nanogaps", Nano Letters, 2010, pp. 420-425.

Nelson, T. et al., Detection of Nucleic Acids with Graphene Nanopores: Ab Initio Characterization of a Novel Sequencing Device, Nano Letters, 2010, pp. 3237-3242.

Ohshiro, T. et al., "Single-Molecule Electrical Random Resequencing of DNA and RNA," Scientific Reports, 2012, pp. 1070-1075.

Sanger, F. et al., "DNA sequencing with chain-terminating inhibitors", Proc. Natl. Acad. Sci. U.S.A. 74, Dec. 1977, pp. 5463-5467.

Schneider, G. et al., "DNA Translocation through Graphene Nanopores," Nano Letters, 2010, pp. 3163-3167.

Tanaka, H. et al., "Partial Sequencing of a Single DNA Molecule with a Scanning Tunnelling Microscope," Nature Nanotechnology, Aug. 2009, pp. 518-522.

Tanaka, H., "Visualization of Detailed Stuctures within DNA," Surface Science, 2003, pp. L531-L536.

Tsutsui, M. et al., "Identifying Single Nucleotides by Tunnelling Current," Nature Nanotechnology, Mar. 21, 2010, pp. 286-290.

University of Pennsylvania. "First step toward electronic DNA sequencing: Translocation through graphene nanopores." ScienceDaily. Jul. 28, 2010, 4 pages. <www.sciencedaily.com/releases/2010/07/100726124418.htm>.

Yarotski, D. et al., "Scanning Tunneling Microscopy of DNA-Wrapped Carbon Nanotubes", Nano Letters, 2009, pp. 12-17.

Zwolak, M. et al., "Electronic Signature of DNA Nucleotides via Transverse Transport." Nano Letters, 2005, pp. 421-442.

NOISE REDUCTION METHODS FOR NUCLEIC ACID AND MACROMOLECULE SEQUENCING

CROSS REFERENCE TO RELATED APPLICATIONS

This patent document claims the benefits and priority of U.S. Provisional Patent Application No. 61/968,280, entitled "NUCLEIC ACID AND MACROMOLECULE SEQUENCING WITH NOISE REDUCTION", filed on Mar. 20, 2014. The entire content of the aforementioned patent application is incorporated by reference as part of the disclosure of this application.

STATEMENT REGARDING FEDERALLY SPONSORED RESEARCH OR DEVELOPMENT

This invention was made with government support under grant DE-AC52-06NA25396 awarded by the U.S. Department of Energy (DOE), along with grant FA9550-10-1-0409, awarded by the Air Force Office of Scientific Research (AFOSR), and along with grant HG002647 awarded by the National Institutes of Health (NIH). The government has certain rights in the invention.

TECHNICAL FIELD

This patent document relates to systems, devices, and processes that use molecular sequencing technologies.

BACKGROUND

Nucleic acid sequencing is the process of determining the precise order of nucleotides within a nucleic acid, such as a DNA molecule or RNA molecule. For example, DNA sequencing has become essential in a variety of biological fields and research. The rapid speed of sequencing has become an important part of biotechnology in diagnostics, forensics, therapeutics, etc., for determining partial or complete nucleic acid sequences, or genomes.

A naturally-occurring double-stranded DNA (dsDNA) includes a linked chain of deoxyribose sugar as a backbone for four nucleotide bases (also referred to as nucleobases), e.g., including adenine (A), cytosine (C), guanine (G), thymine (T). These four nitrogen bases can form hydrogen bonds that hold two individual strands of the DNA together. For example, in naturally-occurring dsDNA, adenine bonds to thymine (A=T) and cytosine bonds to guanine (C≡G). The A=T and CG bonds are two different types of hydrogen bonds formed by the base pairs. Adenine forms two hydrogen bonds with thymine (A=T) and cytosine forms three hydrogen bonds with guanine (C≡G). For example, the energy of formation of N—H . . . O bonds is approximately 8 kJ/mol, and the energy of formation of N—H . . . N bonds is approximately 13 kJ/mol (e.g., where the dotted line represents the hydrogen bond). A naturally-occurring RNA molecule includes a linked chain of ribose sugar as a base for four nucleobases, e.g., including A, C, G, and uracil (U). For example, when RNA binds to DNA, an adenine nucleobase of DNA forms two hydrogen bonds with uracil nucleobase of RNA (A=U). RNA molecules are single stranded and can form many structural configurations.

SUMMARY

Disclosed are systems, devices, and methods for noise reduction in any serial physical property measurement of DNA and other macromolecules to enable sequence determination using oversampling and cross-correlation techniques. In some implementations, for example, the disclosed sequencing data processing methods can be used for increasing the signal-to-noise in DNA sequential measurements including, for example, a nanopore method of nucleic acid sequencing where the current is measured as DNA translocates through a nanopore or nanochannel, and Scanning Tunneling Microscopy techniques that are carried out for electronic and structural characterization of DNA adsorbed on a substrate. The disclosed technology holds great promise for alternative technologies to standard PCR methods that use electronic and other physical property "fingerprints".

In one aspect, a method for processing serial sequencing data includes obtaining a sequencing data set of a macromolecule having a plurality of subunits, in which the obtained sequencing data set includes (i) signal data including multiple measured signals of a physical property of at least some of the subunits of the macromolecule and (ii) time data associated with a corresponding measured signal; determining a signal value for a particular subunit by cross-correlating the multiple measured signals including the time data associated with the corresponding measured signal to remove or at least reduce signal noise that is not in the same frequency and in phase with the systematic signal contribution of the measured signals; repeating the determining the signal value for another subunit of the macromolecule; and generating a data set of the determined signal values.

In one aspect, a system for processing serial sequencing data includes a computer; and a computer readable medium that stores software, that when executed, causes the computer to: obtain a sequencing data set of a macromolecule having a plurality of subunits, in which the obtained sequencing data set includes (i) signal data including multiple measured signals of a physical property of at least some of the subunits of the macromolecule and (ii) time data associated with a corresponding measured signal, determine a signal value for a particular subunit by cross-correlating the multiple measured signals including the time data associated with the corresponding measured signal to remove or at least reduce signal noise that is not in the same frequency and in phase with the systematic signal contribution of the measured signals, and determine additional signal values for other subunits by cross-correlating the multiple measured signals including the time data that corresponds to the measured signals to reduce the signal noise associated with the measured signals of the other subunits, and generate a data set of the determined signal values.

In one aspect, a computer program product comprising a non-transitory computer-readable storage medium having instructions stored thereon and operable to cause a data processing apparatus to perform operations to process serial sequencing data. The operations include receiving a sequencing data set for a macromolecule having a plurality of subunits, in which the received sequencing data set includes (i) signal data including multiple measured signals of a physical property of at least some of the subunits of the macromolecule and (ii) time data associated with a corresponding measured signal; determining a signal value for a particular subunit by cross-correlating the multiple measured signals including the time data associated with the corresponding measured signal to remove or at least reduce signal noise that is not in the same frequency and in phase with the systematic signal contribution of the measured signals; repeating the determining the signal value for another subunit of the macromolecule; and generating a data set of the determined signal values.

In one aspect, a method for macromolecular sequence determination in serial sequencing data includes receiving sequencing data for a macromolecule having a plurality of subunits, in which the sequencing data includes (i) multiple measured signal data values for at least some of the subunits and (ii) time data associated with each corresponding measured signal data value; processing the acquired sequencing data to increase a signal-to-noise ratio (SNR) of the sequencing data, the processing including cross-correlating the multiple measured signal data values for a subunit using the corresponding time data to reduce signal noise that is not in the same frequency and in phase with the systematic signal of the measured signal data value, and cross-correlating the multiple measured signal data values for additional subunits using the corresponding time data to reduce the signal noise in signal data of the additional subunits; and generating a data set of sequencing data with the increased SNR The subject matter described in this patent document can be implemented in specific ways that provide one or more of the following features. For example, the disclosed data processing methods for noise suppression in serial sequencing characterizations can be used in various applications for DNA sequencing, e.g., which are very useful in identifying short DNA fragments, in studies of DNA-pathogen interactions, and for the determination of other macromolecules, among other applications.

DETAILED DESCRIPTION

Figure 1B:
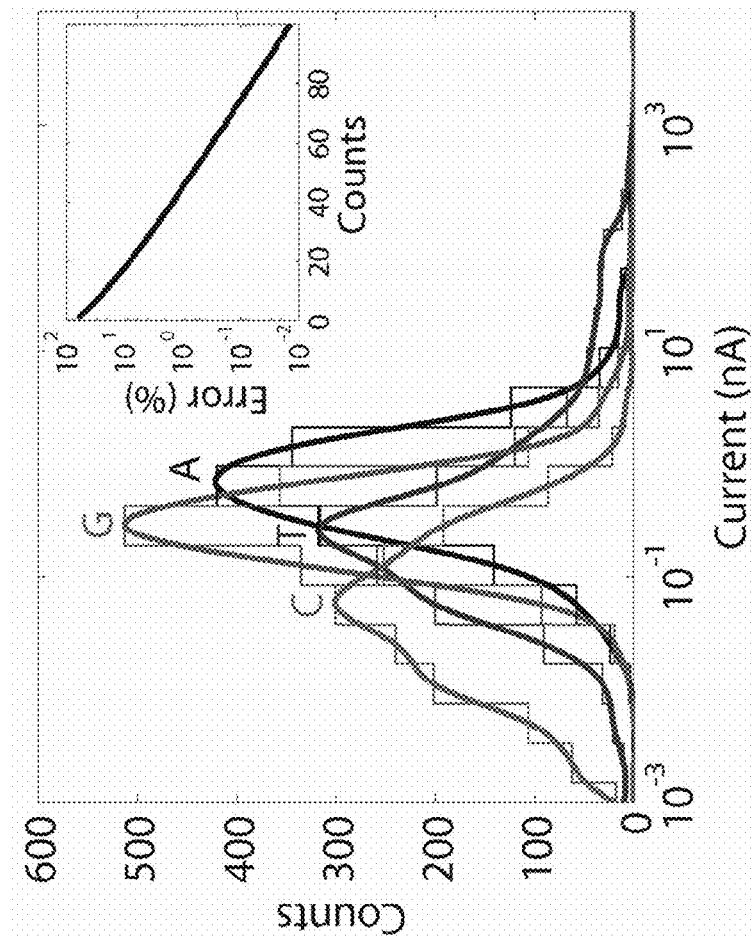
FIG. 1B shows a data plot depicting distributions of currents per nitrogen base of the DNA obtained by translocating homogeneous strands of DNA bases.

Sequencing of macromolecules and especially of DNA is an extremely important area for Biology, Medicine and Pharmacology. Developing realistic inexpensive methods for sequencing is becoming a crucial area for research and technological development. Presently available methods for sequencing are very costly and without much decrease in price, as is envisioned towards the important, desired target cost of about or under $1,000 per human genome. For example, if the cost of DNA sequencing could be reduced to less than $1,000—namely orders of magnitude cheaper than present techniques—this would open up many new areas of science and would foster applications in the field of personalized medicine and pharmaceutics.

To date alternatives to standard PCR sequencing methods that have emerged rely on sequential determination of the genome or macromolecule using serial physical property measurements. One key problem with existing serial physical property sequencing methods is that they are very susceptible to a large number of noise sources, which make their use problematic, perhaps impossible. Therefore development of a noise reduction scheme becomes imperative. The disclosed technology includes methods for noise reduction, which are applicable to any serial measurement, and in particular, for example, to nanopore and scanning tunneling microscopy methods for serial sequencing of macromolecules.

Disclosed are systems and methods to increase the signal-to-noise ratio (SNR) in sequential macromolecular sequencing characterization techniques. The disclosed methods include oversampling and cross-correlation techniques that enable fast, accurate, and cost-efficient sequence determination of structures of macromolecules under detection. Applications of the disclosed technology can be used for reducing or eliminating noise associated with any serial or sequential physical property measurement of macromolecules, e.g., such as various optical, electrical, or chemical serial sequencing techniques. The disclosed technology can be used for such serial sequencing techniques for any type of macromolecule being sequenced, e.g., such as nucleic acids like DNA and RNA, etc. In some implementations, for example, the disclosed methods can be used for DNA sequential measurement techniques including the nanopore method, where current is measured as DNA translocates through a nanopore or nanochannel, and Scanning Tunneling Microscopy (STM) techniques, which are carried out for electronic and structural characterization of DNA adsorbed on a substrate. The disclosed technology holds great promise for alternative technologies to standard Polymerase Chain Reaction (PCR) methods that use electronic and other physical property "fingerprints".

Examples of Serial Sequencing Methods for DNA and Sources of Noise

Sequential determination of the genome relies on a sequential measurement of the DNA bases along the DNA molecule. Two principal methods of such sequential determine include the nanopore method and scanning tunneling microscopy.

Figure 1A:
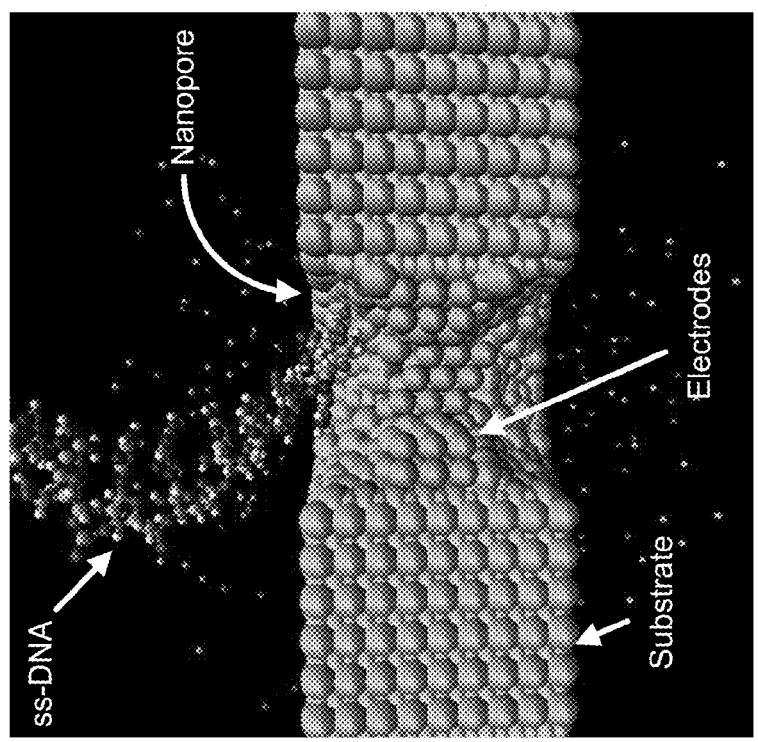
FIG. 1A shows a schematic illustration of an ss-DNA translocating through a nanoscale pore of a substrate with electrodes in a DNA sequencing characterization.

Nanopore Method:

In this approach a pair of electrodes is positioned in proximity to a nanopore or nanochannel, namely a hole of nanoscale dimensions in a solid-state membrane or a long and narrow channel carved out of a surface, respectively. The DNA is then translocated through this opening and the electrodes measure the transverse current distribution of the bases. The distributions of the current are statistically distinguishable but overlapping due to several sources of noise. FIG. 1A shows an illustrative schematic diagram of an ss-DNA translocating through a nanopore and measured with electrodes present in the pore, e.g., represented by yellow atoms, as the ss-DNA translocates. FIG. 1B shows a data plot showing the distributions of currents per base obtained by translocating homogeneous strands of DNA bases.

Figure 2A:
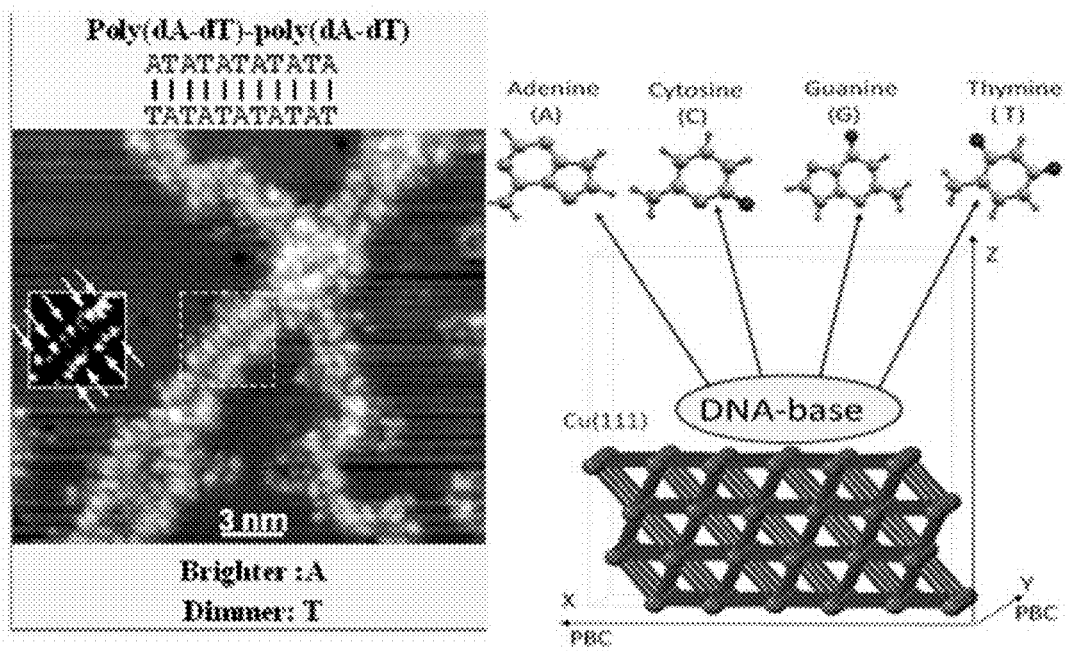
FIG. 2A shows an exemplary image diagram of deposited DNA macromolecules visualized and characterized using Scanning Tunneling Spectroscopy.
Figure 2B:
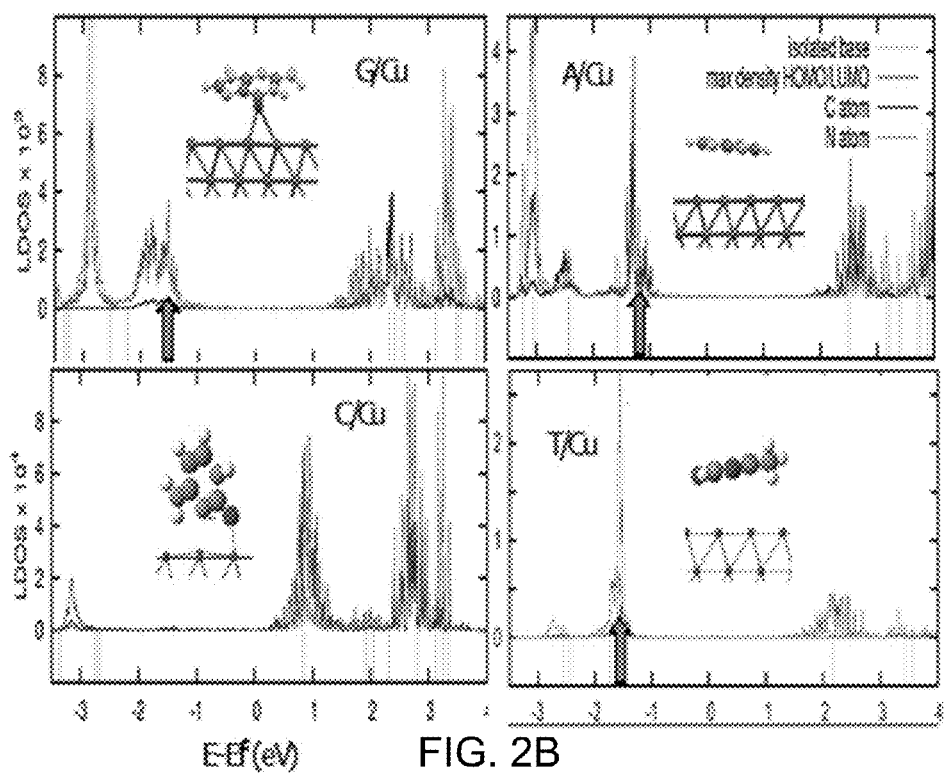
FIG. 2B shows a data plot depicting the calculated spectroscopic features of each base (A, T, G, C).

Scanning Tunneling Microscopy (STM):

In the STM approach, a scanning tunneling microscopy system is used for simultaneous electronic and structural characterization of DNA, RNA and other macromolecules at nanoscale with atomic resolution. The geometry of the macromolecules adsorbed on the substrate surface (e.g., freeze dried) is fixed. STM spectroscopy of the macromolecule on the metal surface reveals the spectroscopic details and fingerprints of molecule. The topographic and spectroscopic results obtained by the STM provide information about individual properties of the constituent structures of the macromolecules, e.g. every one of 4 amino acids A, C, T, G for DNA molecules. FIG. 2A shows an image and diagram depicting deposited macromolecules, which are visualized and characterized using Scanning Tunneling Spectroscopy. FIG. 2B shows calculated spectroscopic features of each base (e.g., A, T, G, C). Significant feature in Local Density of States at −1.5 eV is shown with arrows in the data plots of FIG. 2B.

Noise Sources:

As shown in FIGS. 1A-2B, structural fluctuations of DNA bases in between the electrodes, e.g., due to thermal motion and electron scattering of water, reduces the statistical distinguishability of the bases. In the freeze-dried approach, various conformations of same bases also lead to noisy electronic tunneling signals. Other sources of noise that will influence the current distributions include dephasing due low-energy excitations of electrons scattering off low energy modes of DNA (macromolecule) thermal motion, electron current loss in the liquid, noise due to possible surface rearrangement of atoms the probes induced by either local heating and/or electromigration. In general, for example, the noise sources are randomly spaced in the frequency spectrum without any phase coherence with the expected signal in any sequential measurement.

Exemplary Methodology of the Disclosed Technology

Figure 3:
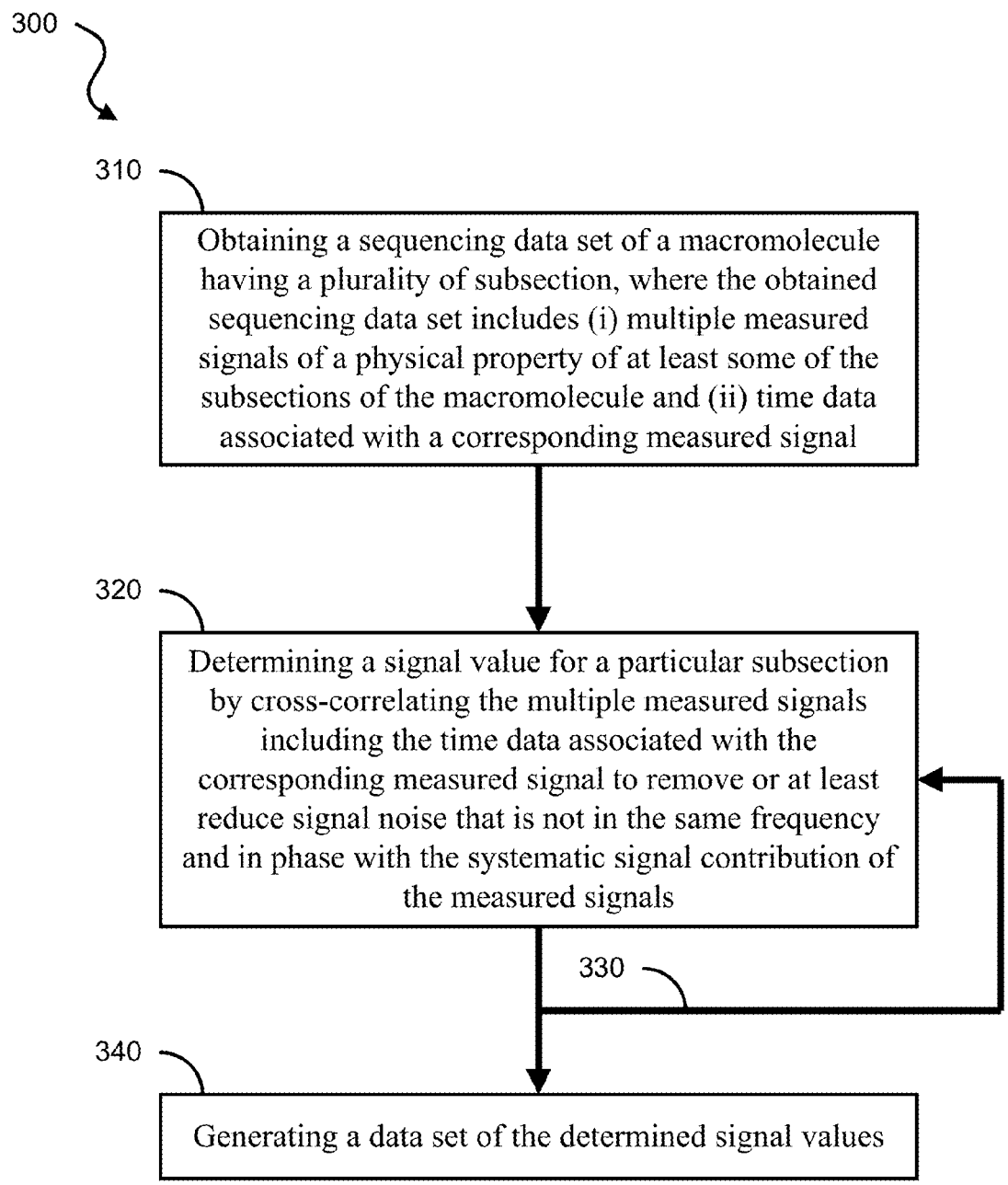
FIG. 3 shows a block diagram of an exemplary data processing method to reduce noise in macromolecule sequencing data.

The disclosed technology includes a phase locking methodology that can reduce, if not eliminate, practically all of the noise which is not in the same frequency and in phase with the measurement. FIG. 3 shows a block diagram of one example embodiment of a data processing method 300 to reduce noise and increase the SNR in macromolecule sequencing data. The method includes a process 310 to obtain a sequencing data set of a macromolecule having a plurality of subunits, in which the obtained sequencing data set includes (i) multiple measured signals of a physical property of at least some of the subunits of the macromolecule and (ii) time data associated with a corresponding measured signal. The method includes a process 320 to determine a signal value for a particular subunit by cross-correlating the multiple signals including the time data associated with the signal data, in which signal noise that is not in the same frequency and in phase with the systematic signal contribution of the measured signals is reduced. The method includes, at 330 in the block diagram, repeating the process 320 to determine the signal value for another subunit (e.g., any other subunit of interest in the obtained sequencing data set). The method includes a process 340 for generating a data set of the determined signal values, in which the data set includes the signal data with an increased SNR and reduced noise.

For example, the subunits of the macromolecule are regions, segments, substructures, or components of the macromolecule. In an illustrative example, the subunits can include substances that form the macromolecule, e.g., such as nucleotide bases of a nucleic acid (e.g., such as DNA or RNA classes of molecules); or amino acids of a peptide, polypeptide, or protein; or monomers of a polymer.

For example, the obtained sequencing data set includes at least three measured signals of the physical property for the subunits of interest. In some implementations of the method, for example, the obtained sequencing data set includes at least ten measured signals per subunit of the macromolecule.

Typically in a sequential technique for DNA sequencing, a physical signature (e.g., resistive, tunneling, optical, etc.) for a particular base is detected in a serial manner. In this fashion the measurement is performed at a well-defined velocity, which can be engineered for a particular method. In the two specific examples mentioned above, either the macromolecule or DNA is moved at a well-defined velocity through a nanopore or an STM tip is moved along an anchored DNA or macromolecule strand. Thus data is acquired at a well-defined velocity and phase.

The disclosed method can utilize simultaneous measurement using multiple measurements (e.g., oversampling of the sequencing measurement data) which have been previously determined, and the known time separation between them. An exemplary model is presented below that illustrates some advantages of the disclosed method, e.g., including multiplexing of the signal on a simple model.

Once the multiple data is acquired, the exemplary process, represented mathematically, can be implemented to provide considerable noise reduction. This includes calculating the multiple cross-correlation between the different measurements using the oversampled data.

Figure 4:
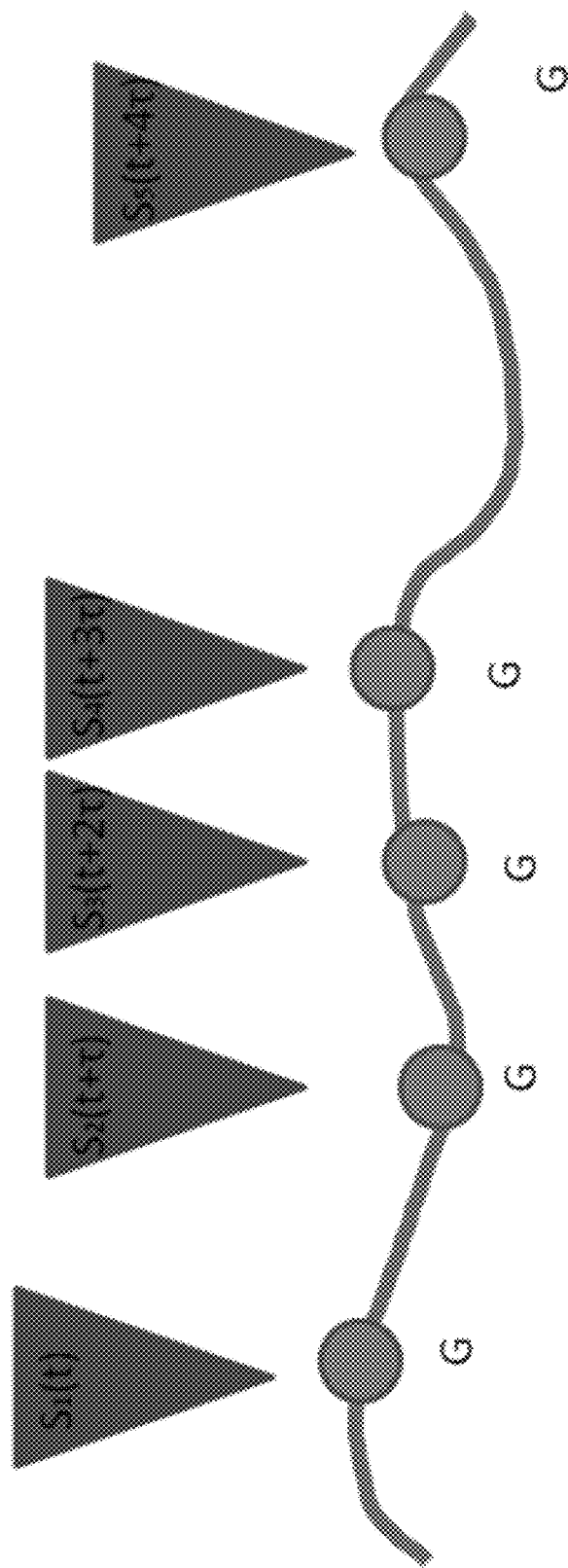
FIG. 4 shows an illustrative diagram of readout channels representing sequencing measurement data for noise reduction using an exemplary method of the disclosed technology.

In this example, a set of readout signals is obtained. For example, these signals can be acquired from multiple nanopores or from multiple read heads in STM. FIG. 4 shows a diagram of multiple readout channels representing sequencing measurement data from multiple read heads using STM for noise reduction using the exemplary method of the disclosed technology. This takes the form as shown in Eq. (1) if the multiple measurements $S_i(t)$ for a given substructure (e.g., readout site) of the macromolecule have the same time delay $\tau$ between them.

$$R(\tau) = \int S_1(t) * S_2(t-\tau) * S_3(t-2\tau) * S_4(t-3\tau) * S_5(t-4\tau) * \ldots S_N(t-(N-1)\tau) dt \quad (1)$$

where $S_i(t)$ is the particular signal measured at time t for the readout signal sample number i.

Now assume signal of readout i=1, 2 . . . N is:

$$S_1(t) = s_1(t) + \sigma_1(t) \quad (2)$$

$$S_2(t) = s_2(t) + \sigma_2(t)$$

$$\ldots$$

$$S_N(t) = s_N(t) + \sigma_N(t) \quad (3)$$

We assume that the signal at each readout is given by the sum of the signal from macromolecule, where $s_i(t)$ stands for systematic signal and uncorrelated noise $\sigma_i(t)$, which is not correlated with the systematic signal s(t). Here i=1–N is the range of readout channels given by number of nanopores or by number of points at which the STM signal is acquired, e.g., as shown in FIG. 4.

Furthermore without loss of generality it can be assumed that noise $\sigma_i(t)$ has zero mean, is uncorrelated in time, and is not correlated between readout sites:

$$<\sigma_i(t)>=0; <\sigma_i(t')\sigma_j(t)>=\gamma\delta_{ij}\delta(t-t') \quad (4)$$

with dispersion $\gamma$.

We then can estimate the correlation function $<S_i(t)S_j(t')>$ as $$<S_i(t)S_j(t')>=<s_i(t)s_j(t')>+<\sigma_i(t')\sigma_j(t)>+<s_i(t)><\sigma_j(t')>+<s_j(t')><\sigma_i(t)> \quad (5)$$

And from Eqs. (4) and (5) we find:

$$<S_i(t)S_j(t')>=<s_i(t)s_j(t')>+\gamma\delta_{ij}\delta(t-t') \quad (6)$$

The last two terms vanish since mean of noise is zero. One can immediately see therefore that for nonzero delay times in Eq. (6) the term proportional to $\gamma$ is on the order unity and vanishes for $|t-t'|>0$. Any noise which is not at the same frequency and in phase with the multiple measurements will be eliminated. Since the noise in all practical cases is expected to be uncorrelated as a function of frequency or outside the frequency range of the measurement, this methodology is a very efficient and effective approach to reduce noise. In this fashion, the signal to noise ratio will increase exponentially. In some implementations of the method, for example, 10 measurements will be sufficient to reduce the noise to make serial measurements feasible.

By implementing the disclosed method on the obtained sequential data set, the resulting data set removes the noise such that only the systematic signal is remaining. For example, if the correlation function from Eq. (6) is used as an input into Eq. (1), we will have only significant contribution from the systematic signal and contribution from the uncorrelated noise drops out from Eq. (1).

Figure 5:
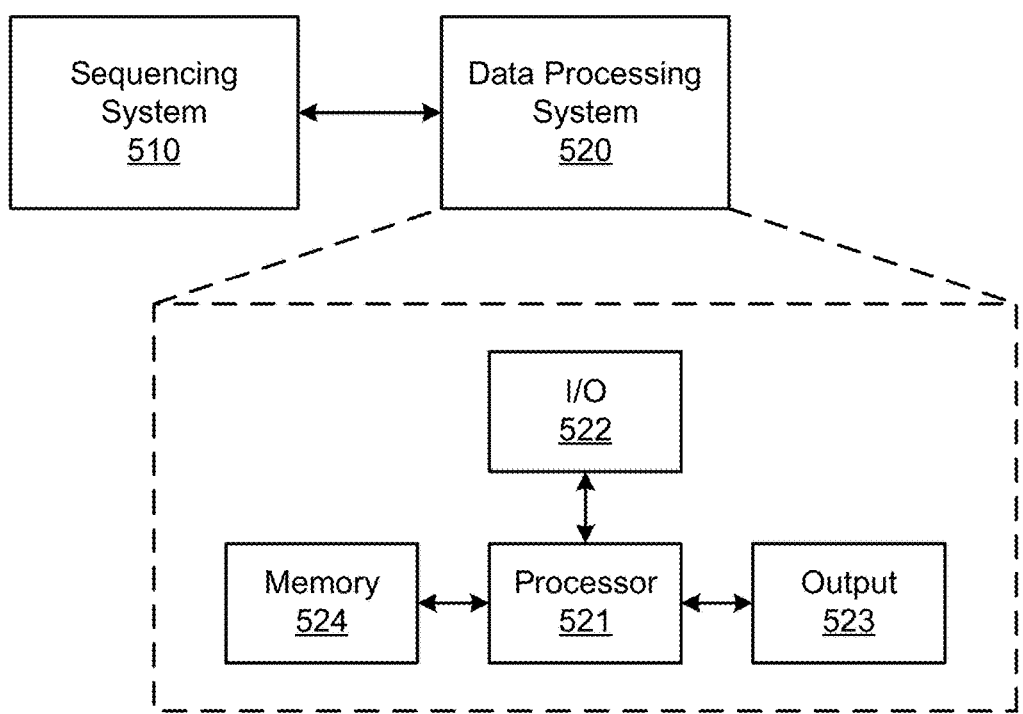
FIG. 5 shows a diagram of an exemplary system to implement the sequencing signal data noise reduction techniques of the disclosed technology.

FIG. 5 shows a block diagram of an exemplary data processing system 520 of the disclosed technology to implement the disclosed methods, e.g., such as the method 300. The data processing system 520 is operable to receive a sequencing data set from a sequencing system 510. In some implementations, for example, the data processing system 520 is in wired or wireless data communication with the sequencing system 510, and in some implementations, for example, the data processing system 520 is included as part of the sequencing system 510. For example, the sequencing system 510 can include an STM system or a nanopore system to acquire sequencing data like that previously shown in FIGS. 1A-2B. The data processing system 520 can include various modules or units for processing the sequencing data set representative of measured signals representative of physical properties detected for the sequential subunits of a macromolecule, e.g., which can be captured from the sample for a nucleic acid or other macromolecule sequencing by the sequencing system 510. The data processing system 520 can implement the disclosed methods, e.g., using the described phase locking techniques, to reduce noise at frequencies and phases not in the same frequency and phase ranges as the sequential measurement of the subunits of the macromolecule (e.g., nucleobases of the DNA or RNA sample). In some implementations, for example, the sequencing system 510 can include systems and devices to implement Nanopore or STM techniques to process the nucleic acid and/or other macromolecule samples.

The data processing system 520 can include a processor 521 that can be in communication with an input/output (I/O) unit 522, an output unit 523, and a memory unit 524. The processing system 520 can be implemented as one of various data processing systems, such as a personal computer (PC), laptop, and mobile communication device, e.g., such as a smartphone or wearable computing device. To support various functions of the data processing system 520, the processor 521 can interface with and control operations of other components of the data processing system 520, such as the I/O unit 522, the output unit 523, and the memory unit 524. In some implementations, for example, the processor 521 can include a central processing unit (CPU), microcontroller, or FPGA.

To support various functions of the data processing system 520, the memory unit 524 can store other information and data, such as instructions, software, values, images, and other data processed or referenced by the processor 521. Various types of Random Access Memory (RAM) devices, Read Only Memory (ROM) devices, Flash Memory devices, and other suitable storage media can be used to implement storage functions of the memory unit 524. The memory unit 524 can store data and information, which can include sample data, and information about other units of the system, e.g., including the sequencing system 510 such as machine system parameters, and hardware constraints, as well as software parameters and programs. The memory unit 524 can store data and information that can be used to implement the disclosed rapid, reduced noise nucleic acid and/or macromolecule sequencing techniques.

To support various functions of the data processing system 520, the I/O unit 522 can be connected to an external interface, source of data storage, or display device. Various types of wired or wireless interfaces compatible with typical data communication standards, such as Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 4G LTE, and parallel interfaces, can be used to implement the I/O unit 522. The I/O unit 522 can interface with an external interface, source of data storage, or display device to retrieve and transfer data and information that can be processed by the processor 521, stored in the memory unit 524, or exhibited on the output unit 523.

To support various functions of the data processing system 520, the output unit 523 can be used to exhibit data implemented by the data processing system 520. The output unit 523 can include various types of display, speaker, or printing interfaces to implement the output unit 523. For example, the output unit 523 can include cathode ray tube (CRT), light emitting diode (LED), or liquid crystal display (LCD) monitor or screen as a visual display to implement the output unit 523. In other examples, the output unit 523 can include toner, liquid inkjet, solid ink, dye sublimation, inkless (e.g., such as thermal or UV) printing apparatuses to implement the output unit 523; the output unit 523 can include various types of audio signal transducer apparatuses to implement the output unit 523. The output unit 523 can exhibit data and information, such as the sample data in a completely processed or partially processed form. The output unit 523 can store data and information used to implement the disclosed rapid, reduced noise nucleic acid and/or macromolecule sequencing techniques.

Exemplary Implementations of the Disclosed Technology

Exemplary implementations of the disclosed data processing methods to increase SNR in macromolecular sequencing data included the physical implementation of the data acquisition methods for the sequencing data, e.g., in which the example implementation is specific to the type of measurement and was engineered in each case separately. Thus for the existing methods mentioned about this would take the following form.

In exemplary implementations using data acquired from the nanopores method, several measurement platforms were stacked on top of each other and a single nanopore/nanochannel was drilled through the combination N platforms. For example, this was performed using a combination of thin film and nanolithography techniques. In this fashion, as the macromolecule (e.g., DNA molecule) was controllably dragged through the nanopore, the various bases sequentially went through each platform that individually monitored the transverse resistance.

In exemplary implementations using data acquired from the STM method, N individual tips were used to measure an electrical signal by following each other for performing transverse tunneling measurements, e.g., as is done in a single measurement. Alternatively, using a single tip, one can use the recorded temporal correlations of the signal as tip moves along the DNA molecule and measures the time delayed correlations of the tunneling current. $<I(t) I(t+\tau)>$ with the delay time $\tau$ chosen to maximize correlation function when one encounters same base at time t and t+$\tau$, t+2 $\tau$, ... etc. This time was sequence dependent and depended on the protocol of STM measurements.

In both of these exemplary methods (and/or other sequential methods), each measurement platform was pre-calibrated with a known macromolecular sequence to enhance reliability.

In some example implementations of the disclosed method, correlation dynamics were explored for enhancing the signals in a data set for serial DNA sequencing, as discussed below.

Nanopore characterization technologies using transverse currents have significant potential for the development of fast, accurate, and cost-efficient finger-printing techniques for next generation DNA sequencing technology. However, the presence of significant noise in the temporal spectrum of transverse current data limits the level of accuracy in the identification of single bases of DNA molecules. Exemplary implementations using the disclosed data processing techniques were performed to overcome this issue, in which the cross-correlations of the sequential measurement of transverse current signal data, as obtained from multiple pairs of electrodes, were processed to enhance the SNR of such measurements. The exemplary implementations include the implementation of first-principles transport calculations for DNA bases probed across an exemplary multilayered graphene nanopores system. The results of the exemplary implementations demonstrated that the cross-correlations of noisy current data between different layers can enhance the transverse current signal, as presented below. For example, a time-series analysis of cross-correlation functions illustrated the potential of the exemplary method for enhancing the signal to noise ratio, thereby allowing for fingerprinting of single biomolecules.

The field of DNA sequencing is rapidly evolving, but is now facing the need for a rapid scale up of accuracy, speed, and resolution for smaller amounts of material. Nanopore-based sequencing and other serial methods provide great promise, particularly for identifying single DNA bases using transverse conductance. Such approaches can rely on the ability to resolve electronic fingerprints of DNA one relevant unit at a time ("serial") while for example, the DNA is translocated in a nanochannel, in the case of the nanopore method. Some experimental methods are capable of achieving single-base resolution, which has allowed the determination of local electrical properties of single DNA bases.

Single-molecule sensitivity of nanopore sequencing can be performed, as well as the sequencing of DNA/RNA oligomers and microRNA by tunneling. Yet, despite such high-quality experimental methods, the most pressing challenge in serial sequencing lies in overcoming effects of noise that lead to a small signal to noise ratio (SNR) in the measured current (I) data. For example, signal fluctuations generally originate from thermal agitation and bond formation between base and nanopore/electrodes wall or interactions with a substrate. Implementations of the disclosed methods can avoid these limitations, e.g., in which the data processing includes cross-correlations of the sequential measurement of transverse current data, obtained from multiple pairs of electrodes.

Figure 6:
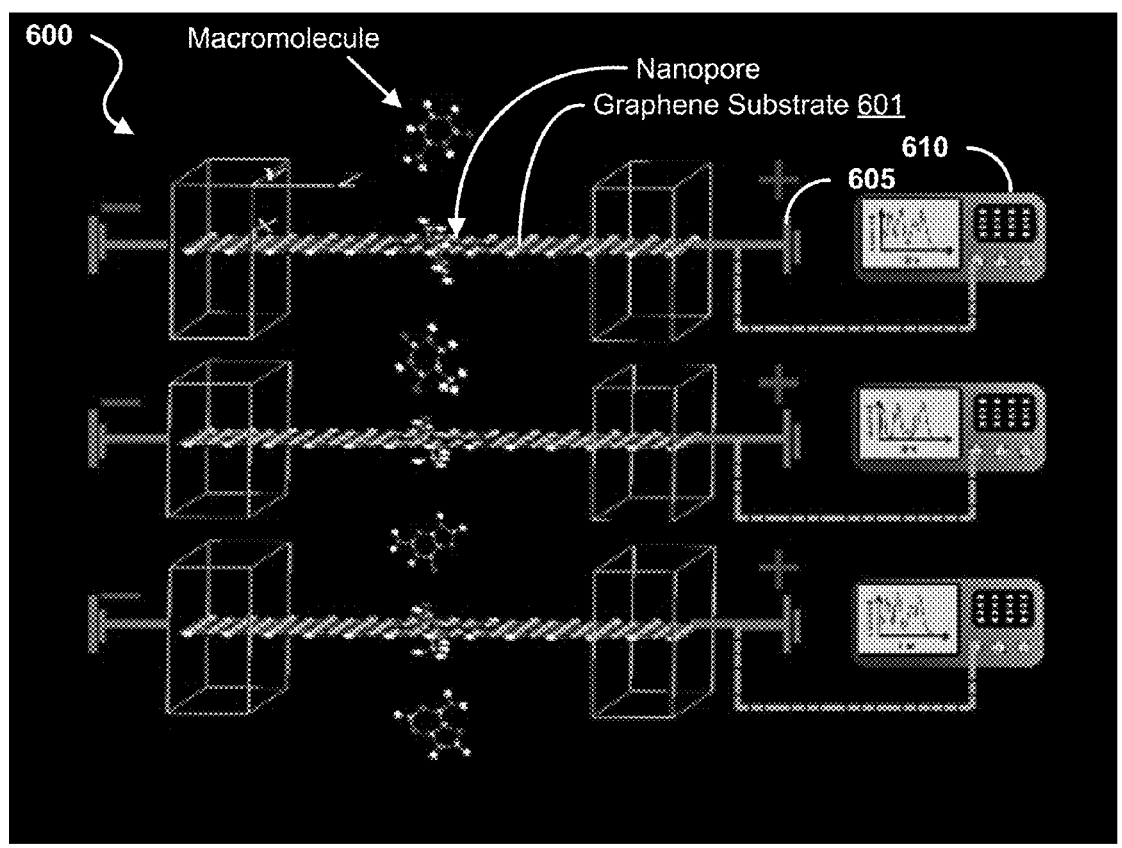
FIG. 6 shows a schematic diagram of a nanopore characterization system for data sequencing of a macromolecule using a nanopore arrangement.

FIG. 6 shows a schematic diagram of a nanopore characterization system 600 setup for data sequencing of a macromolecule using the nanopore arrangement. In the exemplary implementations, graphene was used as the substrate including nanopores, e.g., because it is atomically thick, and exhibits extraordinary thermal and electronic properties. Besides these geometric advantages and good conductivity, graphene also possesses high tensile strength and can survive in high transmembrane pressure. Consequently graphene can be used as an effective substrate and conducting medium for nanopore sequencing. As shown in the schematic diagram of FIG. 6, the nanopore system 600 includes an array of substrates 601 including a pore (e.g., nanopore) through which the macromolecule translocates and is probed by an electrical circuit 605 including at the nanopore to detect an electrical signal indicative of a physical property for each subunit of the macromolecule.

The disclosed methods are useful can be applied to any other macromolecule sequencing method in which serial measurements (e.g., time series) are made to ascertain individual properties of subsections, units, components, regions, etc. of the macromolecule (e.g., resistivity of the bases of DNA, in the examples described for these exemplary implementations).

The nature of an atomically thick graphene nanopore wall cannot completely rule out the $\pi$-$\pi$ stacking between carbon and DNA bases. For example, vibration and other electronic fluctuations present in the graphene membrane can significantly mask the conductance signals, making it difficult to differentiate the individual DNA bases. The interactions between DNA bases and graphene derivatives have revealed the local electronic structure of single bases. The realization of a single layer graphene-based nanopore device is made possible by combining several state of the art techniques e.g., mechanical exfoliation from graphite on $SiO_2$ substrate. Transverse tunneling current (conductance) measurements, as the single strand (ss)DNA translocates through a monolayer graphene nanopore can be performed. AFM studies and theoretical simulations of scanning tunneling spectroscopy (STS) support the identification of electronic features with varying spatial extent and intensity near the HOMO-LUMO band.

Figure 7:
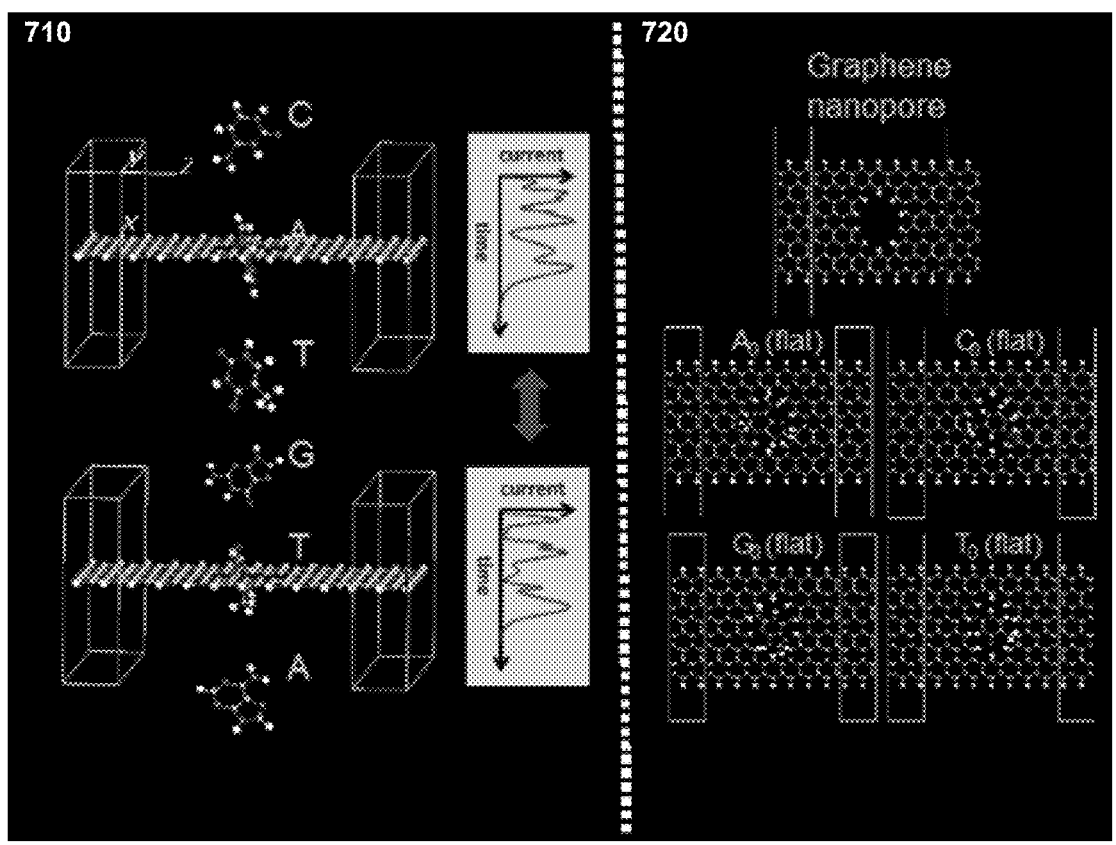
FIG. 7 shows schematic diagrams of transmission currents through two graphene layers where isolated DNA bases pass through the nanopores.

As part of the solution to the noise problem of such systems, a multilayered device is disclosed in which the transverse conductance is measured through each nanopore independently, as a series of DNA bases translocates through them, as depicted in FIG. 7. As molecules translocate, they create a time dependent sequence of translocation currents through each of the layers. The operator can monitor the translocation current at different pores and acquires a record of sequential current of the same base as it arrives and moves through the individual pores. The time series of the cross correlation currents can then be used to reduce the uncorrelated, independent noise sources, and hence enhance the signal to noise ratio and improve the differentiation between bases.

FIG. 7, panel 710, shows a schematic diagram of transmission currents through two graphene layers where isolated DNA bases pass through the nanopores. The current vs. time spectra were recorded for each layer independently. The cross-correlation between the current data from multipores revealed useful base information by increasing the signal to noise ratio. FIG. 7, panel 720, shows an illustrative diagram depicting the hydrogen capped graphene nanoribbons and the DNA bases inside the pore. In the panel 720, only the flat orientation of the DNA bases is shown.

It is noted, for example, that in the exemplary implementations of the disclosed methods using the exemplary nanopore characterization system, as depicted in FIGS. 6 and 7, the background contribution from the large phosphate backbone typically present in a single stranded DNA (ssDNA) was ignored. This simplification was based on the assumption that by identifying and subtracting the background noise coming from the heavy and rigid backbone structure, one can isolate the relevant signal from the individual bases. The exemplary implementations included building a model of the pore conductances containing a molecule in two steps by: (1) first, carrying out ab initio calculations of transmission (T(E)) and current (I) as a single DNA bases translocate through the nanopore of a graphene mono-layer; and (2) then, simulating the time-dependence of the current data by adopting a simple model with multilayered graphene nanopores with added statistical noise and broadening.

The exemplary implementations included calculations of transmission, taking each DNA base inside the nanopore with three different angular orientations, and using the Landauer-Buttiker formalism that was implemented in ab initio software ATK. It is noted that the disclosed methods do not rely nor require a geometry optimization of molecules in the pores. The translocation is a dynamical process with significant variations of configurations found for molecules inside a pore. Thus, the same molecule can arrive in different orientations at each pore, a process which contributes to the configuration noise sources that are addressed. Therefore, no optimization of the configurations was performed. The set of various configurations can be used as the set from, which the random sampling is taken.

In these example calculations of the exemplary implementations, utilized was a graphene nanoribbon with 208 carbon atoms in the conduction region, where the nanopore was constructed by removing center carbon atoms and capping the inner wall with hydrogen atoms, e.g., since hydrogenated edges were found to enhance the average experimental conductivity. The bias voltage between the left and right electrodes was fixed as +0.35 and −0.35 eV. The nanopore dimension was much smaller than other models of such. The details and various parameters of the exemplary first-principles calculations are described later.

To demonstrate the recoverability of current I(t) signals from noise, the relation between noise coming from different layers is shown. For simplicity, it was considered that the dominant noise primarily from two sources. As the bases translocate through the i-th graphene nanopore layer, the vibration in the DNA backbone may influence individual base plane to land with random angular orientation with the graphene plane, causing a configuration-noise $S_i^C(t)$. The additional noise, such as thermal vibration of the graphene membrane at the i-th nanopore, is defined as $S_i^A(t)$. Thus the total noise of i-th nanopore can be expressed as:

$$S_i(t) = S_i^C(t) + S_i^A(t). \quad (X1)$$

The correlation function between the two layers is therefore given by:

$$\langle S_i(t) \cdot S_j(t') \rangle = \langle S_i^C(t) \cdot S_j^C(t') \rangle + \langle S_i^C(t) \cdot S_j^A(t') \rangle + \langle S_i^A(t) \cdot S_j^C(t') \rangle + \langle S_i^A(t) \cdot S_j^A(t') \rangle \quad (X2)$$

Here $t' = t + \Delta t$. For $i \neq j$, the contribution from the last three terms on the right-hand side of Eq. X2 are negligible due the weakly or uncorrelated signals in separate nanopores. Since the DNA bases are strongly attached to the ssDNA backbone, the configuration-noise between two membranes mainly contributes to the first term in Eq. X2. Therefore, the noise can be approximated as:

$$\langle S_i(t) \cdot S_j(t') \rangle \approx \langle S_i^C(t) \cdot S_j^C(t') \rangle, \quad (X3)$$

where, for i=j, all terms on right side of Eq. X2 survive and contribute significantly to the total noise. Since the noise between i and j is uncorrelated, a comparison of their signals will enhance the individual base signals by reducing the noise to signal ratio.

For example, there are two extreme limits that can be taken advantage of based on the above observation. These limits relate to the rate of base translocation compared to typical vibrational frequency of the bases facing the electrodes. When this occurs, the above cross correlations allow us to reduce the intrinsic noise due to random orientations. On the other hand, when the translocation rate is slower than the vibrational frequency, the uncorrelated noise is eliminated and the only one that survives is the correlated one. Here, in these exemplary implementations, the second case is focused on, e.g., since experimentally the latter situation is more likely.

Figure 9:
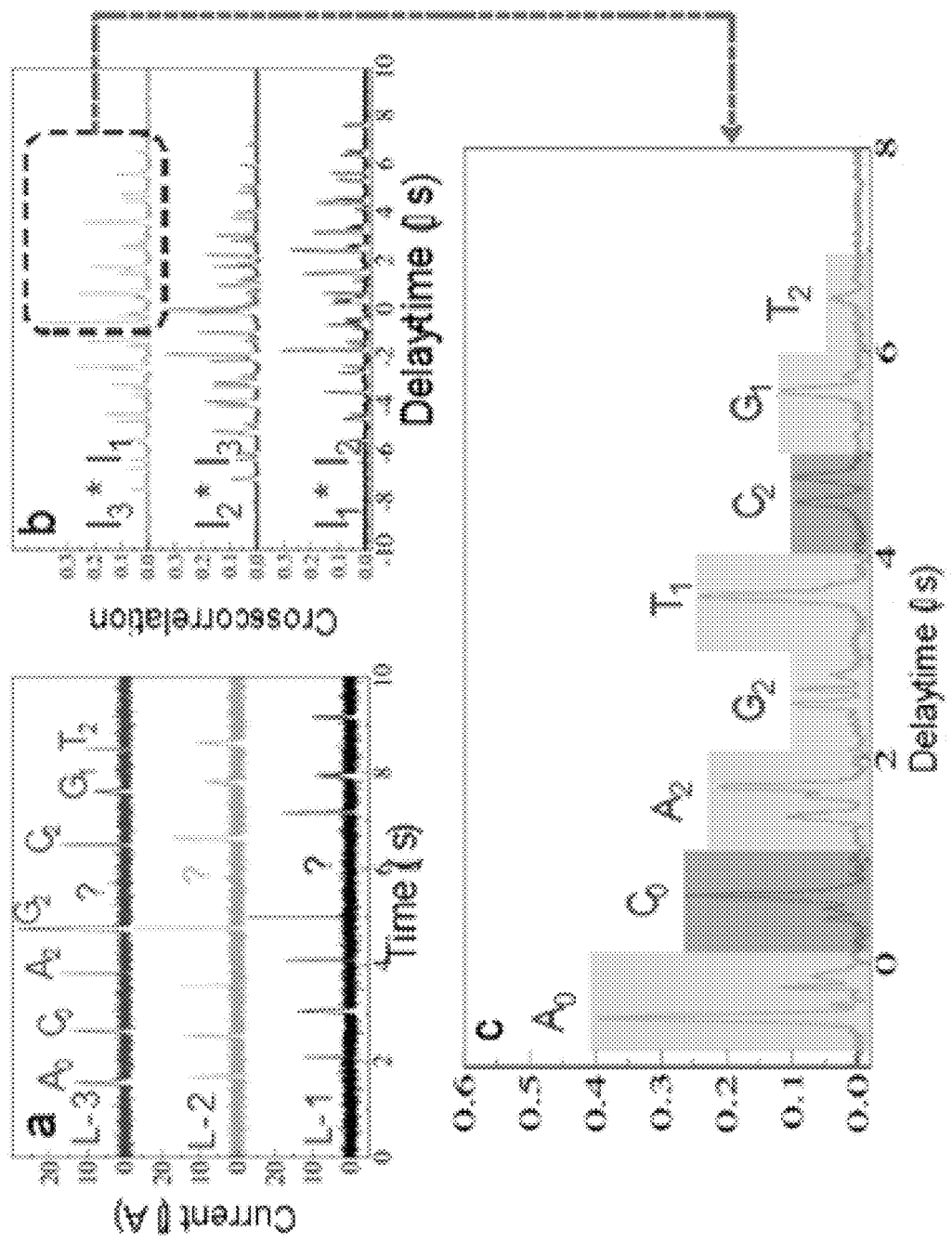
FIG. 9 shows data plots depicting the partial signal recovery using an exemplary time-simulation model.

As an example, the low current amplitude for Thymine is shown in FIG. 9 panel (a), and in FIG. 9 panel (c) the enhancement of the signal to noise ratio. A test sequence $A_0C_0A_2G_2T_1C_2G_1T_2$ was taken, where the subscripts imply different angular orientations of the bases inside the pore. The time dependence of this sequence is modeled by taking the time interval between two consecutive bases $\tau = 1.0$ μs, including a random Gaussian uncertainty between the interval with $\sigma_\tau = \pm 0.2$ μs. Each current signal is also broadened using a random Gaussian broadening with $\sigma_{broad} = \pm 0.2$ μA. To simulate a realistic experiment with background noise, additive white Gaussian noise was also included. It was assumed that with the applied field in the vertical direction, the average elapsed time between two translocating bases is $\tau = 1.0$ μs. The time-distance between two consecutive graphene layers is set to $\Delta t \approx 0.2$ μs.

Exemplary results of these example calculations are described. For example, the first-principles calculations of transmittance for individual DNA bases inside the graphene nanopore are presented in FIG. 8. FIG. 9 shows the partial signal recovery using our time-simulation model with three layer graphene nanopores and the cross-correlation between the corresponding signals.

Figure 8:
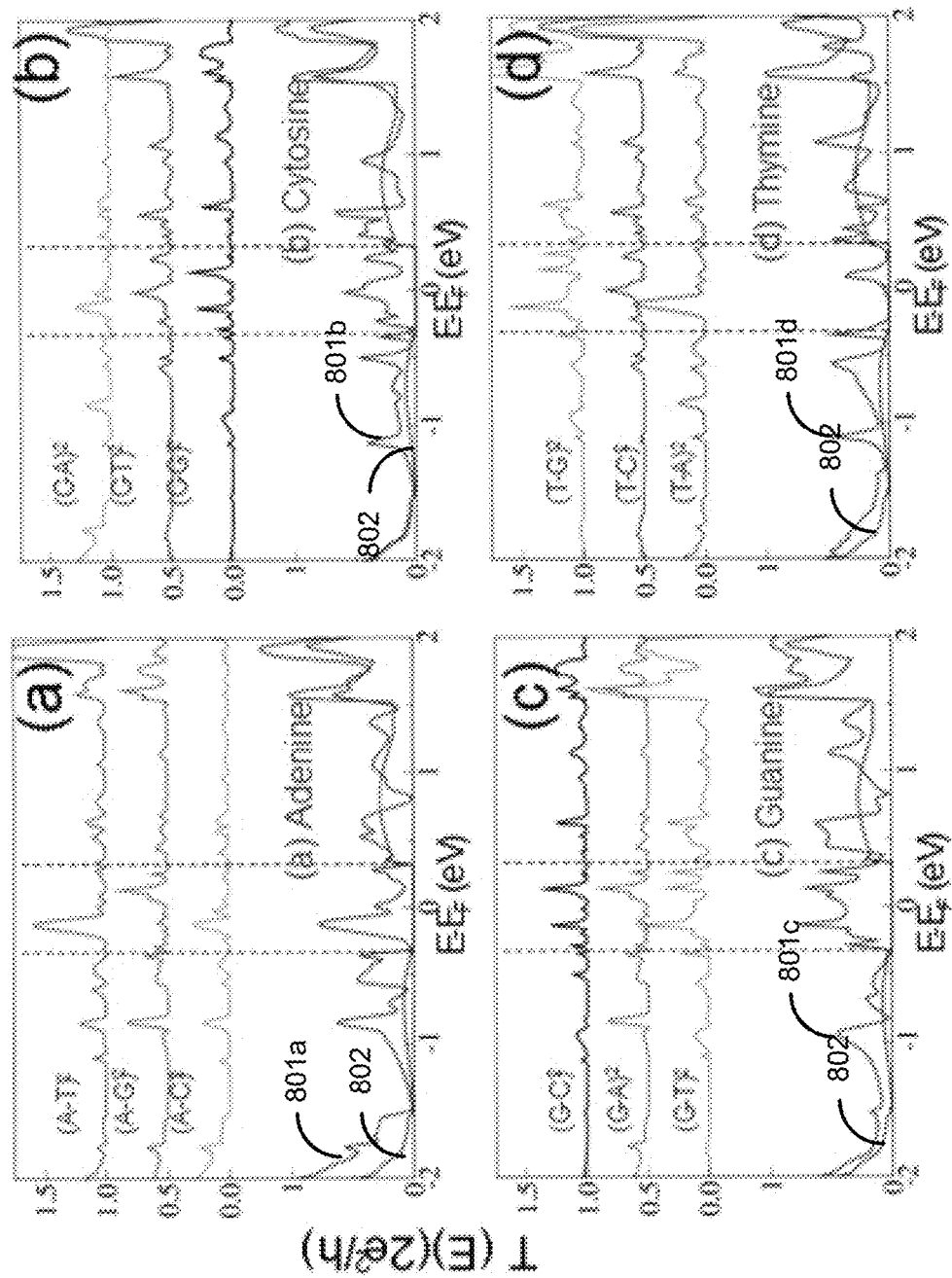
FIG. 8 shows data plots of exemplary transmittance data for individual DNA bases inside the exemplary graphene nanopore characterization system.

FIG. 8 shows data plots of example configuration averaged transmission coefficients (solid blue lines 801a, 801b, 801c, 801d) for (a) Adenine, (b) Cytosine, (c) Guanine, and (d) Thymine. The solid red line 802 is T(E) for pure graphene with the nanopore for comparison. The vertical dashed lines are at −0.35 eV and +0.35 eV, which are the chemical potentials EF of the left and right electrodes respectively. The top three curves in each panel (a), (b), (c), and (d) are the difference-square curves between the average T(E) for each base. The Fermi energy of the central region is at 0 eV, and the difference curve shows the distinguishing features for each of the DNA bases.

FIG. 9 panel (a) shows a data plot depicting current vs. time (μs) data for a translocating DNA sequence 'ACAGTCGT' for three graphene layers labeled as L-1, L-2, and L-3. An additive white noise is included in the current spectrum. For example, due to high noise to signal ratio some of the spectral features become harder to recognize (indicated by a question mark in the figure). FIG. 9 panel (b) shows a data plot depicting the cross-correlation between current signals I1(t), I2(t), and I3(t) as functions of delay time t, where the currents are from grapheme layers L-1, L-2, and L-3 respectively. FIG. 9 panel (c) shows a data plot depicting an enlarged segment of the cross-correlation function from FIG. 9 panel (b). These correlation-signal peaks correspond to the peaks from current-signal for the DNA sequence ACAGTCGT.

In the example first-principles approach, for each DNA base, three random angular orientations were taken with the graphene membrane, while calculating the transmittance between the two electrodes with 0.7 V bias voltage. The configuration averaged transmittance for A, C, G, and T are shown in the data curve 801a, 801b, 801c, and 801d for the respective four bases, as shown in in FIG. 8. The conductance of a pure graphene nanoribbon with hydrogenated nanopore is shown in the data curve 802 in the multiple panels of FIG. 8 for comparison. The transmittance curve is analogous to the non-equilibrium density of states in the presence of the bias voltage, where the zero of energy is the Fermi energy of the central graphene region. The vertical dashed lines at −0.35 eV and +0.35 eV are the chemical potentials of the left and right electrodes, respectively. For each base shown in FIG. 8, the transmittance curve (solid blue line 801) in between the left and right electrode chemical potentials is significantly enhanced compared to the pure graphene membrane with a nanopore (solid red line 802). The features in this region are characteristic of the four bases. For example, a comparison of the Guanine transmittance (FIG. 8 panel (c)) with that of Thymine (FIG. 8 panel (d)), shows the presence of a characteristic broad peak.

For a systematic study of the difference between the transmittance among the four bases, the difference curves (the top three curves) were plotted. If the signatures of one or more of the DNA bases are known prior to the detection, the difference curves may provide the signature of an unknown base. For example, if one knows the transmittance of Thymine a comparison of the characteristic features of difference-squared transmittance $(A-T)^2$, $(G-T)^2$, $(C-T)^2$, helps identify the unknown base. FIG. 8 panels (a), (c), and (d) show that the difference-curves contain several (up to three) dominant peaks in between the vertical dashed lines. These characteristic peaks originate from the three different angular orientations calculated here. In principle, it is possible to calculate a large number of configurations and maintain a complete data-base of such characteristic difference curves for the sequencing purpose.

Such methods are challenged by two major limitations. The first one is prior knowledge of the exact location of one or more DNA bases, either from the transmittance curve or from other technique. The second one is the presence of significant noise in the data, which makes it difficult for the detection of any single base. Some bases exhibit characteristic features in the transmittance curve, which make them easily detectable. For example, Thymine (FIG. 8 panel (d), solid blue line curve 801d) has very low conductance compared to the others, e.g., shown by the low peak amplitude near 0 eV. However, even the detection of Thymine can be difficult in the presence of noisy data. To illustrate the specifics of the approach, the simulation of a time-series for three graphene nanopore layers with the test sequence $A_0C_0A_2G_2T_1C_2G_1T_2$ is shown in FIG. 9.

In the exemplary implementations of the nanopore based DNA sequencing, the current I(t) was the measured quantity rather than the transmittance T(E). Thus, the current was calculated from the transmittance. Using the parameters described in this patent document, the time-dependent current spectra $I_{L-1}$, $I_{L-2}$, and $I_{L-3}$ was simulated for the example test sequence, as shown in FIG. 9 panel (a). The low current amplitude for Thymine in the case of $T_I$ and $T_2$ is expected from the transmittance curve in FIG. 8 panel (d), but the natural noise present in the data makes it difficult to confirm the presence of $T_1$ at the expected location. As shown in FIG. 9 panel (b), the cross-correlation between the current spectra from different pairs of graphene layers is presented. For each pair, the cross-correlation was plotted as a function of time-delay within the −10 μs to +10 μs range. The cross-correlation spectrum was approximately symmetric around the mid-point of the total range due to the overlaps between similar pairs of peaks from opposite ends of the original data. Therefore, the positive time-delay was focused on. The correlation spectrum inside the highlighted dashed box in FIG. 9 panel (b) was enhanced and rotated in FIG. 9 panel (c). By comparing peaks between FIG. 9 panels (a) and (c), the presence of Thymine with $T_1$ configuration was confirmed. Although the amplitudes of the current spectrum do not translate directly into the amplitudes of the cross-correlation spectrum, they confirm the existence of $T_i$. Thus, a time-series analysis using current cross-correlations $\langle I_i(t) \otimes I_j(t) \rangle$ recovers all eight peaks in the example test sequence (FIG. 9 panel (b)). The suppression of white noise is substantial and the peaks at time-delay=0 in the correlation function (FIG. 9 panel (b)) are enhanced.

This approach can be extended to three-point or higher N-point correlations, which is demonstrated here, for example, to exponentially reduce the noise-to-signal ratio. The two-point cross-correlation is generally expressed with a single parameter as in Equation X4:

$$R^2(\tau) = \int_0^T I_1(t) I_2(t-\tau) dt, \tag{X4}$$

where the time interval is between 0 and T. The three-point correlation is a function of two independent variables:

$$R^3(\tau, \tau') = \int_0^T I_1(t) I_2(t-\tau) I_3(t-\tau') dt \tag{X5}$$

Figure 10:
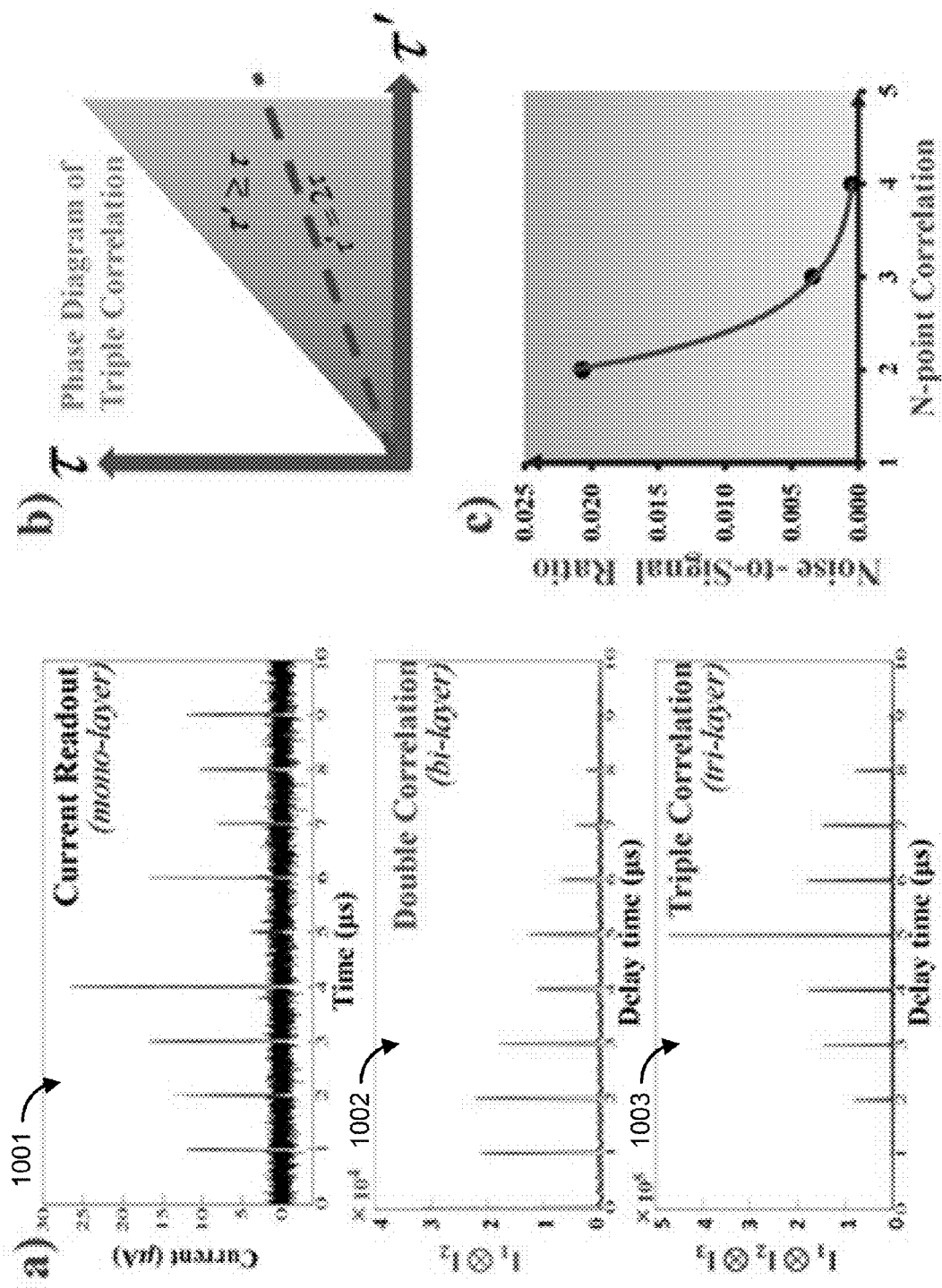
FIG. 10 shows data plots featuring example processed sequencing data depicting the improvements in signal-to-noise ratio with higher order cross-correlation.

For example, the description of triple correlation function can be simplified in the complete two dimensional parameter space by constraining it to the line τ'=2τ as in FIG. 10 panel (b). Thus the constrained triple correlation function becomes:

$$R^3(\tau) = \int_0^T I_1(t)I_2(t-\tau)I_3(t-2\tau)dt \qquad (X6)$$

Following this example procedure, currents can be measured from N independent graphene layers, and one can calculate constrained the N-point correlation as:

$$R^N(\tau) = \int_0^T I_1(t)I_2(t-\tau)I_3(t-2\tau) \ldots I_N(t-(N-1)\tau)dt \qquad (X7)$$

FIG. 10 panel (a) shows three data plots including example data depicting the improvements in signal-to-noise ratio with higher order cross-correlation. Time dependent current spectrum for the sequence $A_0C_0A_2G_2T_1C_2G_1T_2C_1$ from a single layer graphene is shown in the top plot 1001 (black); where the double and triple cross-correlated spectra are shown in the middle plot 1002 (red), and bottom plot 1003 (blue). FIG. 10 panel (b) shows an exemplary phase diagram of a triple correlation function on a 2D delay-time parametric space for t and t'. The dashed red line is our constraint for calculating the triple correlation function. FIG. 10 panel (c) shows an exemplary data plot depicting the nearly exponential decay of noise-to-signal ratio with higher order correlation.

The three data plots in FIG. 10 panel (a) show the exemplary calculated current signal from a single layer as well as the two and three point cross-correlation functions from the corresponding two and three independent graphene nanopores. The test sequence used in these example implementations is $A_0C_0A_2G_2T_1C_2G_1T_2C_1$. Using two, three and four point cross-correlation functions, the ratios between the average signal and average noise in each case were estimated, as shown in Table 1. The example data shown in FIG. 10 panel (c) confirmed the exponential drop in the noise to signal ratio. The computational details and the table containing the results are described later in this patent document.

For example, in such cases with extremely noisy data, the noise can highly screen the small signals arising from weakly conducting bases such as Thymine. When the requirement for an accurate and exact location of a certain DNA base in the sequence becomes essential, one can incorporate more graphene layers and thus more cross-correlation functions between them. For example, a six by six two-point cross correlation matrix certainly carries more information, such as in FIG. 9.

Figure 11:
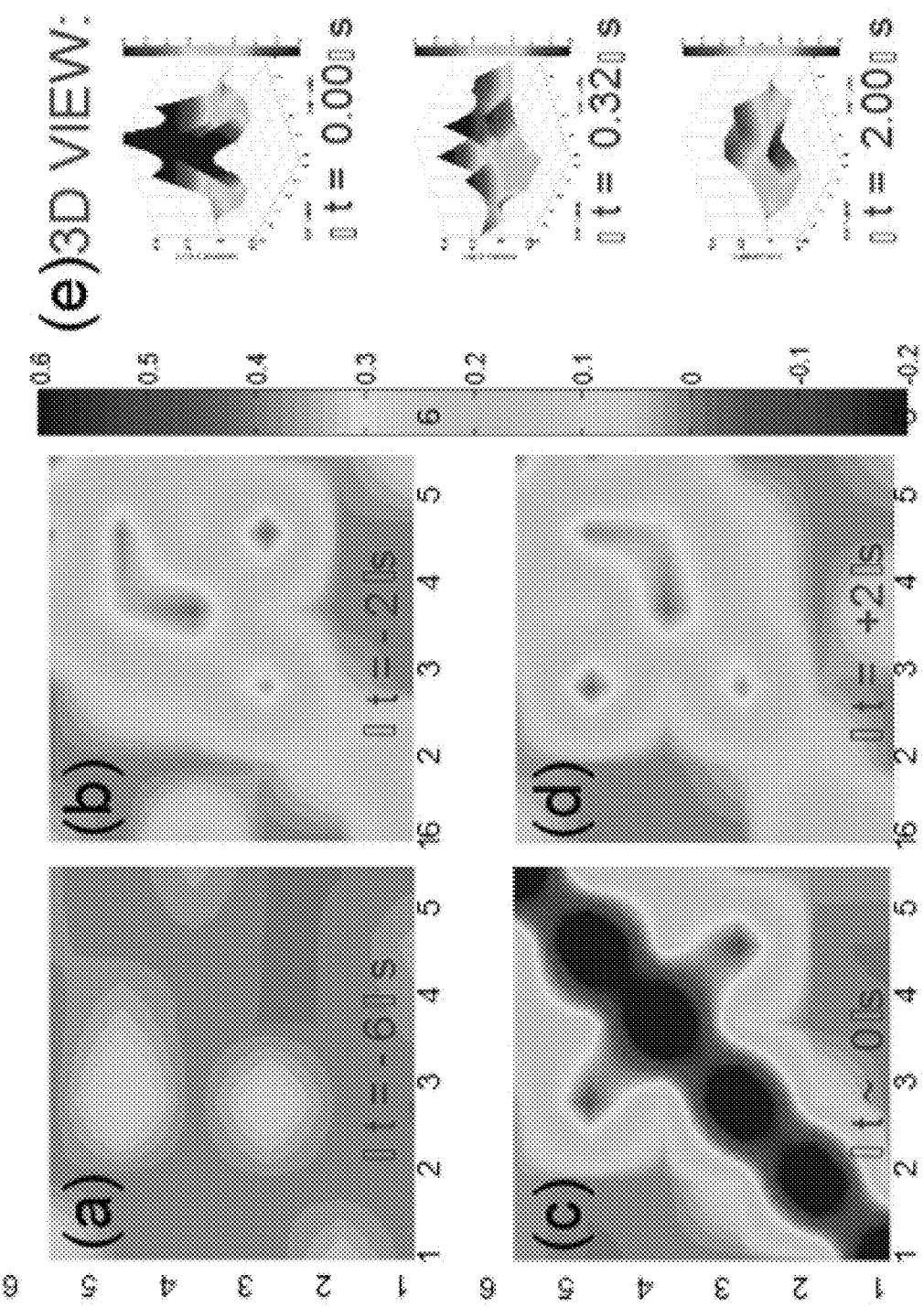
FIG. 11 shows plots depicting an example correlation matrix as a function of delay time for six graphene nanopore layers.

FIG. 11 panels (a)-(d) show four example snap shots of the 2-D contour plots of cross-correlation matrix at delay times $\Delta t = -6, -2, 0$, and $+2$ μs. For example, a reflection symmetry is present between $=-2$ μs, and $=+2$ μs, which can also be seen from comparing FIG. 11 panel (b) and FIG. 11 panel (d). To improve visual perspective by smoother contour plots, the cross-correlation matrix was interpolated on the xy plane. FIG. 11 panel (e) shows a 3D snap shots of delay times $\Delta t = 0, 0.32$, and $2.00$ μs, showing a 3D projected surface plot for the correlation matrix where the z axis represents the value of the cross-correlation function.

For example, as discussed in relationship to FIG. 9, the cross-correlation spectrum enhances the signal to noise ratio and helps recover particular weak signals. It is noted that the exemplary data presented in FIG. 11 is qualitative and limited to only four time slices. Further illustration of the disclosed techniques including a time evolution of the six by six correlation matrix is also discussed.

These exemplary implementations have demonstrated use of the disclosed methods for enhancing the signal in the identification of translocating single DNA bases through graphene nanopores, e.g., using first-principles calculation of transmittance and cross-correlation techniques. In some implementations, for example, to eliminate the high background noise, a multilayered graphene based nanopore device combined with the exemplary cross-correlation method can be used to substantially improves the signal to noise ratio of the electronic readout of bases. To illustrate this, a statistical approach for simulating the time-dependent current spectrum was adopted, in which the enhanced resolution was produced by the multiple translocation readouts of the same bases of the same molecule through the pores. The cross-correlated signals from each pair of electrodes suppress the uncorrelated noise produced by each single translocation event. In implementations, as discussed above, for example, Thymine can serve as a "reference base" for identifying other bases from the difference transmittance curves. The exemplary implementations also showed the recovery of signals associated with different configurations by taking cross-correlations between different pairs of graphene layers. Thus, the disclosed methods for an enhanced signal to noise ratio can be applied in the multipore graphene based devices or any other serial sequencing device, and are applicable as a next generation DNA sequencing technique.

Additional information regarding the exemplary implementations and acquired and analyzed data is discussed here. An example computational method for calculating triple-correlation functions is described. In the example, three data sets $X_n$, $Y_n$, and $Z_n$ each with size N ($=10000$), and each includes white Gaussian noise caused by the apparatus, was included. The two-point cross-correlation function can be computed as:

$$R^2(m) = \sum_{n=0}^{N-1-m} X_{n+m}Y_n \text{ for } m \geq 0 \qquad (X8)$$
$$= \sum_{n=0}^{N-1+m} X_n Y_{n-m} \text{ for } m < 0.$$

Similarly an unconstrained triple (three-point) correlation is obtained from:

$$R^3(m, q) = \sum_{n=0}^{N-1-m} X_{n+m}Y_{n+q}Z_n \text{ for } m > q \geq 0, \qquad (X9)$$

and all other cases of m and q.

For the special case where $m=2q$, the correlation functions is defined as:

$$R^2(q) = \sum_{n=0}^{N-1-2q} X_{n+2q}Y_{n+q}Z_n \text{ for } q \geq 0 \qquad (X10)$$
$$= \sum_{n=0}^{N-1+2q} X_n Y_{n-q}Z_{n-2q} \text{ for } q < 0$$

Table 1 shows the Average Signal ($\bar{S}$), average noise ($\bar{N}$), and noise-to-signal ratio ($\bar{r}$) for 2, 3, and 4 point cross-correlation functions. For the example test sequence $A_0C_0A_2G_2T_1C_2G_1T_2C_1$, the average signal is calculated as $$\bar{S} = \sum_{i=1} s_i/9,$$

and average background noise was estimated as $\bar{N}=n_{max}/2$.

TABLE 1

| N-point Corr. | $\bar{S}$ | $\bar{N}$ | $\bar{r} = \bar{N}/\bar{S}$ |
|---|---|---|---|
| 2 | $1.453 \times 10^4$ | 302 | 0.02078 |
| 3 | $1.463 \times 10^5$ | 497 | 0.00339 |
| 4 | $2.530 \times 10^6$ | 1198 | 0.00047 |

Single-particle scattering theory is described. Briefly, the key ideas of the first-principles single-particle scattering method are described. In order to calculate transport current, the central physical quantity to be determined is the transmission coefficient T(E). A central (contact) region and two bulk (electrode) regions are typically referred to as a two probe problem. In the presence of bias-voltage between two electrodes one self-consistently calculates the Hamiltonian and self-energy in the bulk region using standard DFT formalism. Thus $H_{RR}$, $H_{LL}$, $\Sigma^R$, and $\Sigma^L$ are determined and remain fixed. Periodic boundary conditions are assumed in these DFT calculations. Now that one has the solutions for the electrodes, the Green's function $G_{CC}(E)$ in the central region is written as:

$$G_{CC}(E)=[EI-H_C-\Sigma^L-\Sigma^R]^{-1} \quad (X11)$$

where I is the identity matrix and HC is the Hamiltonian in the central region. From this Green's function and previously calculated self-energies, the density matrix in the contact region can be determined by doing the following complex contour integrals, $$\bar{D} = \frac{1}{\pi}\int_{-\infty}^{\mu L} G(E)\text{Im}[\Sigma^L]G(E)^\dagger dE + \frac{1}{\pi}\int_{-\infty}^{\mu R} G(E)\text{Im}[\Sigma^R]G(E)^\dagger dE \quad (X12)$$

From this density matrix one calculates the electron density:

$$n(\vec{r}) = \sum_{ij} D_{ij}\phi_i(\vec{r})\phi_j(\vec{r}), \quad (X13)$$

where $\varphi_i(\vec{r})$ are the solutions of the Kohn-Sham equation. Now as the Green's function is calculated self-consistently in the contact region, the transmission coefficient T(E) is calculated. Using the Fermi-distribution function $n_F(E)$, the total current can be calculated by:

$$I = \frac{e}{h}\int_{-\infty}^{+\infty} T(E)[n_F(E-\mu_L)-n_F(E-\mu_R)]dE \quad (X14)$$

In the exemplary implementations, a punctured graphene nano-ribbon suspended between two electrodes was taken. The inner wall of the nanopore is hydrogen capped to avoid any transient bond formation between the translocating bases and carbon atoms. For the device geometry, a two-probe system was employed with the electrodes and the contact region. The bias voltage between the electrodes was set to be 0.7V. For electrodes 100 k points were taken, where for the contacts a gamma-point calculation was performed. The calculations were performed using LDA approximation and PZ functional. Double zeta polarized LCAO basis were used for all atoms. In the central region the complex integral was performed using 1.5 Ha as the lower bound. Pulay mixing algorithm with damping factor 0.1 was used for the SCF cycles. All transport calculations were performed using ATK (Atomistic Toolkit) software.

It was assumed that DNA bases translocate through identical and independent graphene layers. For a single layer, current was calculated for each of the DNA bases with different angular orientations inside the pore. In order to simulate the noise generated from experiments, an additive white noise was included to the signatures of the given sequence 'ACAGTCGT'.

The disclosed technology includes several other additional advantages, e.g., including: 1) oversampling increases the number of measurements thus increasing the statistical significance of the measurement, b) the noise will average out, c) several other schemes includes calculating the cross correlations with nτ delays and d) changing the time delay τ and the phase.

Disclosed are methods and devices/systems physically implementing said methods, for noise reduction in any serial physical property measurement of DNA and other macromolecules that enables sequence determination. In some of the methods of the disclosed technology, noise reduction in sequential measurement utilizes simultaneous measurement using multiple measurements ("oversampling") which have previously determined, known time separation between them. For example, the disclosed methods can utilize a phase locking methodology which reduces practically all the noise which is not in the same frequency and phase ranges as the measurement. The disclosed technology can be implemented in applications for the development of alternatives to standard PCR methods that use electronic and other physical property "fingerprints".

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for processing serial sequencing data acquired using a nanopore system or a scanning tunneling microscopy (STM) system, comprising:
   acquiring, using the nanopore system or the scanning tunneling microscopy (STM) system, signal data from a macromolecule having a plurality of subunits, the acquiring including sequentially measuring signals from at least some of the subunits of the macromolecule at a defined velocity and phase to create a known time separation ($\tau$) between measurements, wherein the acquired signal data includes multiple measurements of the sequentially measured signals from measured subunits of the macromolecule that form a sequencing data set of the macromolecule;
   obtaining, at a data processing unit, the sequencing data set of the macromolecule, wherein the obtained sequencing data set includes (i) a signal amount associated with a physical property of the measured subunits of the macromolecule for each of the multiple measurements and (ii) time data associated with each measured signal of the multiple measurements;
   reducing signal noise in the sequencing data set, at the data processing unit, by determining a signal value for a particular subunit of the measured subunits by cross-correlating the multiple measured signals including the signal amount and the time data to remove or at least reduce signal noise that is not in the same frequency and in phase with the systematic signal contribution of the measured signals, wherein the reduced signal noise includes one or more of thermal motion of the subunits, electron current loss from the subunits to a liquid, or atomic rearrangements at the subunits induced by localized heating or electromigration;
   repeating, at the data processing unit, the determining the signal value for another subunit of the macromolecule; and
   generating, at the data processing unit, a data set of the determined signal values.

2. The method of claim 1, wherein the subunits of the macromolecule include nitrogen bases of a nucleic acid; amino acids of a peptide; or monomers of a polymer.

3. The method of claim 1, wherein the obtained sequencing data set includes at least three measured signals associated with the physical property for the measured subunits.

4. The method of claim 1, wherein, for the nanopore system, the sequencing data set includes electrical signal data of the subunits of the macromolecule translocated through a pore of a substrate having electrodes in the pore to measure an electrical property of the subunits.

5. The method of claim 1, wherein the sequencing data set includes electrical or optical signal data of the subunits of the macromolecule measured by the scanning tunneling microscopy (STM) system or by measuring an electronic signal from the nanopore system.

6. The method of claim 1, wherein the sequentially measuring the signals includes simultaneously measuring the signals from multiple subunits of the same macromolecule.

7. A system for processing serial sequencing data, comprising:

a data acquisition system, including a nanopore system or a scanning tunneling microscopy (STM) system, to acquire signal data from a macromolecule having a plurality of subunits by sequentially measuring signals from at least some of the subunits of the macromolecule at a defined velocity and phase to create a known time separation ($\tau$) between measurements, wherein the data acquisition system is configured to acquire multiple measurements of the sequentially measured signals from measured subunits of the macromolecule that form a sequencing data set of the macromolecule;

a computer comprising a processor and memory, the computer configured to reduce signal noise in the serial sequencing data by obtaining the sequencing data set of the macromolecule, wherein the obtained sequencing data set includes (i) a signal amount associated with a physical property of the measured subunits of the macromolecule for each of the multiple measurements and (ii) time data associated with each measured signal of the multiple measurements, reducing signal noise in the sequencing data set by determining a signal value for a particular subunit of the measured subunits by cross-correlating the multiple measured signals including the signal amount and the time data to remove or at least reduce signal noise that is not in the same frequency and in phase with the systematic signal contribution of the measured signals, and repeating the determining additional signal values for other measured subunits, wherein the reduced signal noise includes one or more of thermal motion of the subunits, electron current loss from the subunits to a liquid, or atomic rearrangements at the subunits induced by localized heating or electromigration, and generating a data set of the determined signal values.

8. The system of claim 7, wherein the subunits of the macromolecule include nitrogen bases of a nucleic acid; amino acids of a peptide; or monomers of a polymer.

9. The system of claim 7, wherein the obtained sequencing data set includes at least three measured signals associated with the physical property for the measured subunits.

10. The system of claim 7, wherein the physical property includes an electrical property, an optical property, or a mechanical property of the subunits of the macromolecule.

11. A system for processing serial sequencing data, comprising:

a nanopore system including a substrate having a nano-sized channel, and at least one pair of electrodes positioned proximate to the nanochannel, wherein the nanopore system is configured to acquire signal data from a macromolecule having a plurality of subunits by sequentially measuring electrical signals from at least some of the subunits of the macromolecule, as the macromolecule is translocated through the nanochannel, at a defined velocity and phase to create a known time separation ($\tau$) between measurements, wherein the nanopore system is configured to acquire multiple measurements of the sequentially measured signals from measured subunits of the macromolecule that form a sequencing data set of the macromolecule;

a computer comprising a processor and memory, the computer configured to reduce signal noise in the serial sequencing data by:

obtaining the sequencing data set of the macromolecule, wherein the obtained sequencing data set includes (i) a signal amount associated with a physical property of the measured subunits of the macromolecule for each of the multiple measurements and (ii) time data associated with each measured signal of the multiple measurements, reducing signal noise in the sequencing data set by determining a signal value for a particular subunit of the measured subunits by cross-correlating the multiple measured signals including the signal amount and the time data to remove or at least reduce signal noise that is not in the same frequency and in phase with the systematic signal contribution of the measured signals, and repeating the determining additional signal values for other measured, wherein the reduced signal noise includes one or more of thermal motion of the subunits, electron current loss from the subunits to a liquid, or atomic rearrangements at the subunits induced by localized heating or electromigration, and generating a data set of the determined signal values.

12. The system of claim 11, wherein the subunits of the macromolecule include nitrogen bases of a nucleic acid; amino acids of a peptide; or monomers of a polymer.

13. The system of claim 11, wherein the obtained sequencing data set includes at least three measured signals associated with the physical property for the measured subunits.

14. The system of claim 11, wherein the physical property includes an electrical property, an optical property, or a mechanical property of the subunits of the macromolecule.

15. The system of claim 11, wherein the nanopore system is configured to simultaneously measure the electrical signals from multiple subunits of the same macromolecule.

* * * * *